(12) United States Patent
Arindam et al.

(10) Patent No.: US 10,800,801 B2
(45) Date of Patent: Oct. 13, 2020

(54) CRYSTALLINE PLATINUM-BASED COMPOUNDS

(71) Applicant: AKAMARA THERAPEUTICS, INC., Philadelphia, PA (US)

(72) Inventors: Sarkar Arindam, New Delhi (IN); Gavin Pringle, Peebles (GB); Jonathan Loughrey, Edinburgh (GB); Saurabh Chitre, Midlothian (GB); Hayley Reece, Dalkeith (GB); Attilia Figini, Rancate (CH); Ivan Ruggiero, Giornico (CH)

(73) Assignee: AKAMARA THERAPEUTICS, INC., Philadelphia, PA (US)

( * ) Notice: Subject to any disclaimer, the term of this patent is extended or adjusted under 35 U.S.C. 154(b) by 0 days.

(21) Appl. No.: 16/302,352

(22) PCT Filed: May 18, 2017

(86) PCT No.: PCT/IB2017/052940
§ 371 (c)(1),
(2) Date: Nov. 16, 2018

(87) PCT Pub. No.: WO2017/199201
PCT Pub. Date: Nov. 23, 2017

(65) Prior Publication Data
US 2019/0345180 A1    Nov. 14, 2019

(30) Foreign Application Priority Data
May 18, 2016   (IN) .............................. 201611017192

(51) Int. Cl.
*C07F 15/00* (2006.01)
*A61P 35/00* (2006.01)
(52) U.S. Cl.
CPC .......... *C07F 15/0093* (2013.01); *A61P 35/00* (2018.01); *C07B 2200/13* (2013.01)
(58) Field of Classification Search
CPC .................................................. C07F 15/0093
See application file for complete search history.

(56) References Cited

U.S. PATENT DOCUMENTS 10,426,753 B2 * 10/2019 Roy ................... A61K 39/3955

FOREIGN PATENT DOCUMENTS

| WO | 2014/201376 A2 | 12/2014 |
| WO | 2015/153345 A1 | 10/2015 |
| WO | 2016/185402 A1 | 11/2016 |

* cited by examiner

*Primary Examiner* — Golam M Shameem
(74) *Attorney, Agent, or Firm* — BakerHostetler

(57) ABSTRACT

The present disclosure relates to pharmaceutical sciences and chemical sciences. In particular, the present disclosure provides crystalline platinum-based compound IO-125, compositions and formulations comprising the same, along with method of preparing said crystalline compound, and uses thereof.

23 Claims, 18 Drawing Sheets

IO-125

CRYSTALLINE PLATINUM-BASED COMPOUNDS

CROSS-REFERENCE TO RELATED APPLICATIONS

This application is the National Stage of International Patent Application No. PCT/IB2017/052940, filed May 18, 2017, which claims the benefit of Indian Patent Application No. 201611017192, filed May 18, 2016, the disclosures of which are incorporated herein by reference in their entireties.

TECHNICAL FIELD

The present disclosure is directed to crystalline forms of platinum-based compounds. Disclosed herein is a crystalline form of IO-125 and methods of making the crystalline form thereof. Extensive studies were performed including initial characterization of the compound IO-125, approximate solvent solubility and bench scale crystallization screening ranging at least between 20-250 mg scale. Crystalline IO-125, can be further formulated as nanoparticles and pharmaceutical compositions. The crystalline IO-125 and the corresponding nanoparticles or pharmaceutical compositions may be used as therapeutic agents in the treatment of diseases and disorders, including, for example, cancer.

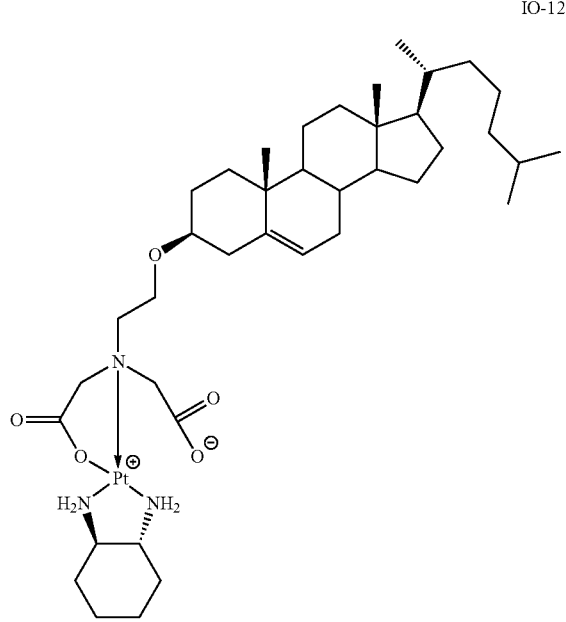

IO-125

BACKGROUND

Generally, crystalline forms of drugs are preferred over amorphous forms of drugs in pharmaceutical industry as amorphous forms of drugs are usually unstable in the environmental conditions such as temperature, humidity, air, and the likes. Further, as amorphous forms of drugs are susceptible to moisture absorption, the solvents that can be used in processing preparations are limited to those which are anhydrous. This can additionally cause an increase in manufacturing costs. Furthermore, maintenance of chemical stability, solid state stability, and "shelf life" of the active ingredients is an important requirement in drug development to demonstrate a reliable, reproducible and constant plasma concentration profile of drug when it is administered to a patient. These parameters can be achieved better with crystalline form of drugs. Also, through crystalline form, it is possible to provide a drug in a form which is as chemically pure as possible. Consequently, in the manufacture of commercially viable and pharmaceutically acceptable drug compositions, it is important, wherever possible, to provide drug in a substantially crystalline and stable form. However, preparation of crystalline form is highly challenging and not always an achievable goal. Typically, it is not possible to predict, from molecular structure alone, what the crystallisation behaviour of a compound will be. This can usually only be determined empirically. More particularly, it is highly challenging to derive crystals of complex molecular compounds such as lipid functionalized platinum based drugs.

Synthesis of various platinum based conjugates/drugs are known in the art. However, as mentioned above, demerits associated with amorphous form of drugs necessitate the need exists for crystalline forms of such complex molecular structures having superior physicochemical properties that may be used advantageously in pharmaceutical processing and compositions. The present disclosure addresses the aforesaid needs of prior art.

SUMMARY

The present invention describes crystalline form of IO-125. Also provided are methods for preparing the crystalline form of IO-125, nanoparticles containing crystalline IO-125, pharmaceutical compositions of crystalline IO-125 or said nanoparticles, and methods of using the crystalline form of IO-125, nanoparticle or pharmaceutical compositions thereof to treat or prevent various diseases.

The present disclosure thus provides a crystalline Form 1 of IO-125

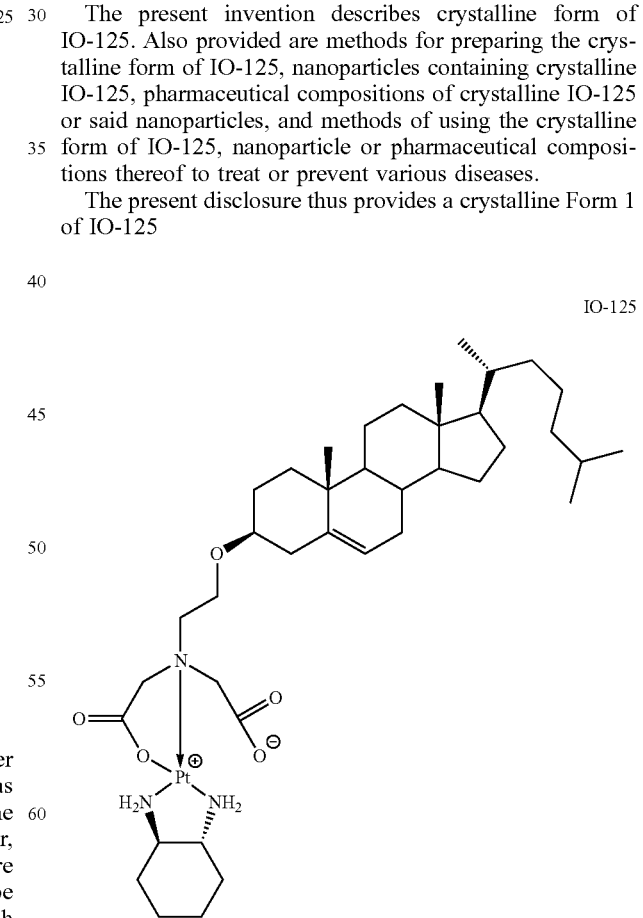

IO-125 a method for preparing a crystalline Form 1 of compound IO-125, comprising (i) preparing a solution of IO-125 by dissolving crude IO-125 in a solvent(s),
(ii) crystallizing the product from the solution, and
(iii) optionally repeating step (ii);
a method for preparing crystalline Form 1 of compound IO-125, comprising
(i) preparing a solution of IO-125 by dissolving crude IO-125 in an organic acid and a halogenated hydrocarbon solvent mixture,
(ii) adding lower alkyl alcohol to the solution to obtain a solution 2, and
(iii) crystallizing the product from said solution 2;
a nanoparticle comprising crystalline Form 1 of compound IO-125;
a pharmaceutical composition comprising crystalline Form 1 of compound IO-125, or a nanoparticle of crystalline Form 1 of compound IO-125, along with excipient(s);
a method of treating or managing cancer in a subject, the method comprising administering a therapeutically effective amount of a crystalline Form 1 of compound IO-125, or a nanoparticle of a crystalline Form 1 of compound IO-125, or a composition of a crystalline Form 1 of compound IO-125 to a subject in need thereof;
use of a crystalline Form 1 of compound IO-125 or a nanoparticle of a crystalline Form 1 of compound IO-125, or a composition of a crystalline Form 1 of compound IO-125 in the manufacture of a medicament for treating cancer selected from a group comprising breast, head and neck, ovarian, testicular, pancreatic, oral-esophageal, gastrointestinal, liver, gall bladder, lung, melanoma, skin, sarcoma, blood, brain, glioblastoma, tumor of neuroectodermal origin and combinations thereof; and
a crystalline Form 1 of compound IO-125 a nanoparticle of a crystalline Form 1 of compound IO-125, or a composition of a crystalline Form 1 of compound IO-125 for use as a medicament in the treatment of cancer selected from a group comprising breast, head and neck, ovarian, testicular, pancreatic, oral-esophageal, gastrointestinal, liver, gall bladder, lung, melanoma, skin, sarcoma, blood, brain, glioblastoma, tumor of neuroectodermal origin and combinations thereof.

BRIEF DESCRIPTION OF THE DRAWINGS

In order that the invention may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure.

DETAILED DESCRIPTION

The present disclosure addresses the challenges of the prior art and provide crystalline forms of platinum-based compounds.

The present disclosure relates to crystalline forms of IO-125

IO-125

As disclosed herein, the terms referring to the compound of the disclosure "IO-125", "Compound 25" and "COMP 25" are used interchangeably.

The crystalline Form 1 of compound IO-125 of the present disclosure has an X-ray powder diffractogram pattern having characteristic peaks at diffraction angles 2θ of 3.16, 6.34, 12.95, 15.55, 16.45, 17.4, 21.56 and 21.92°.

The crystalline Form 1 of compound IO-125 of the present disclosure is further characterized by powder X-ray diffraction substantially as shown in FIG. 4, FIG. 5, FIG. 10, FIG. 13 and FIG. 16 herein.

Figure 15:
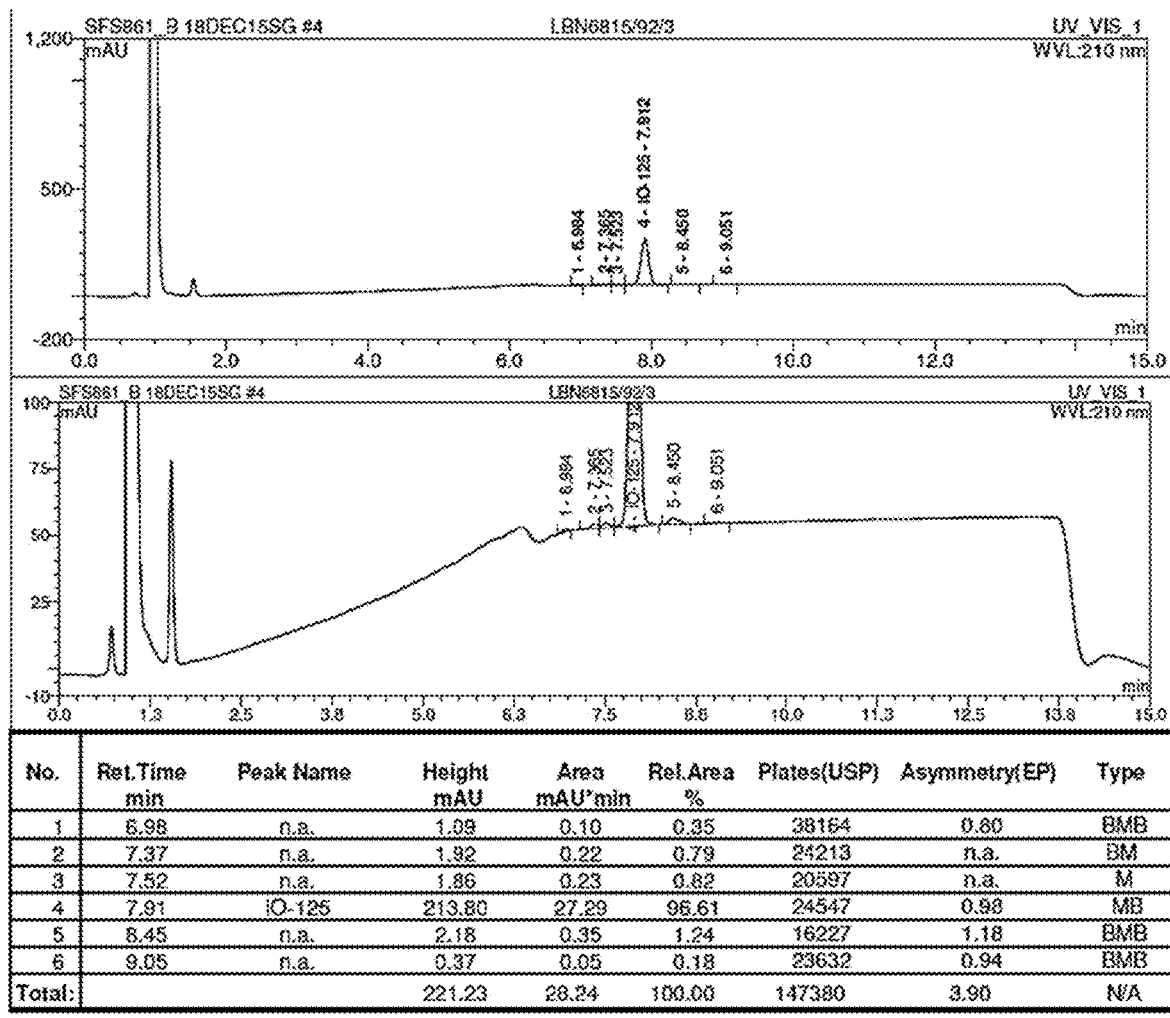
FIG. 15 shows HPLC chromatogram of an isolated solid using methanol:dichloromethane (20:80% v/v) with heptanes as anti-solvent obtained by way of protocol 8.
Figure 17:
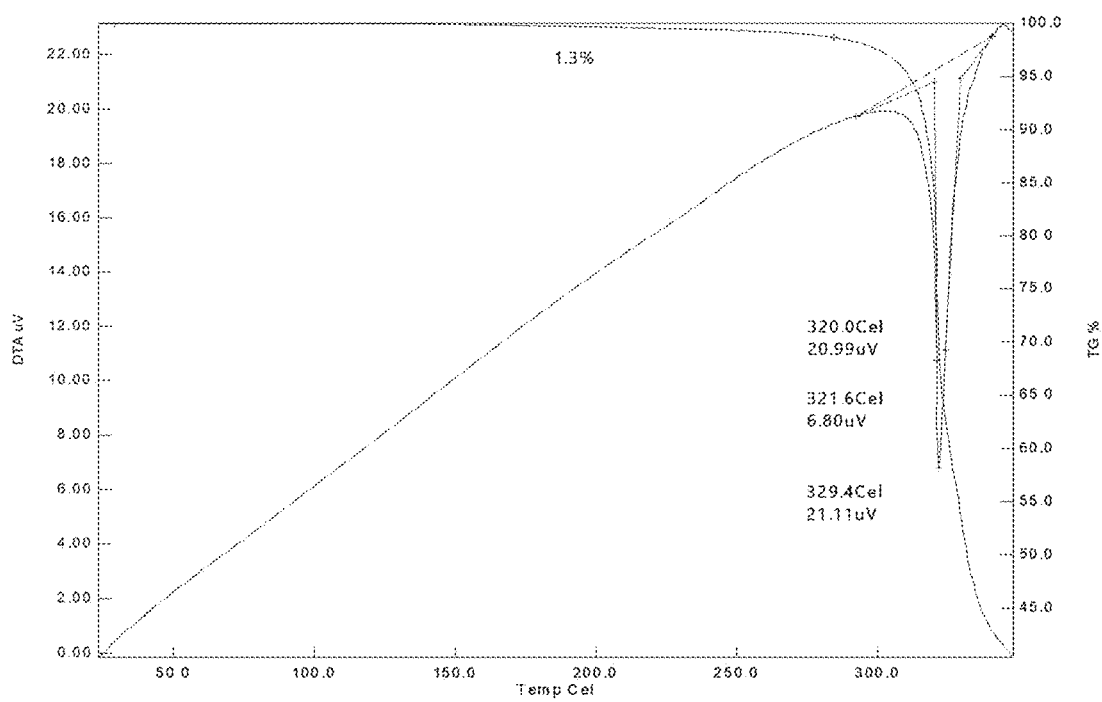
FIG. 17 shows IO-125, Form 1 TG/DTA thermogram (TG trace—blue; DT trace—green).

The crystalline Form 1 of compound IO-125 of the present disclosure is also characterized by thermogram substantially as shown in FIG. 17, or chromatogram substantially as shown in FIG. 15.

In an embodiment of the present disclosure, the melting onset/melting point of the crystalline Form 1 of IO-125 is about 320° C.

In another embodiment of the present disclosure, the crystalline Form 1 of IO-125 has high HPLC purity of about 96.7%.

The present disclosure relates to a method for preparing a crystalline Form 1 of compound IO-125, comprising
(i) preparing a solution of IO-125 by dissolving crude IO-125 in a solvent(s);
(ii) crystallizing the product from the solution; and
(iii) optionally repeating step (ii).

In an embodiment of the present disclosure, the solvent(s) is selected from a group consisting of lower alkyl alcohol, halogenated hydrocarbon solvent, inorganic solvent, organic solvent and combinations thereof.

In another embodiment of the present disclosure, the lower alkyl alcohol is selected from a group consisting of methanol, ethanol, propanol, isopropanol, butanol, iso-butanol, pentanol, iso-pentanol and combinations thereof; the halogenated hydrocarbon solvent is selected from a group consisting of dichloromethane, chloroform and a combination thereof; the inorganic solvent is selected from a group consisting of water; the organic solvent is dimethylformamide, and combinations thereof.

In yet another embodiment of the present disclosure, the solvent(s) is a mixture selected from a group consisting of methanol and dichloromethane, methanol and chloroform, ethanol and dichloromethane, ethanol and chloroform, and combinations thereof.

In still another embodiment of the present disclosure, the solvent(s) is a mixture selected from a group consisting of methanol and dichloromethane having a concentration ratio from about 10:90 to 90:10, by volume; methanol and chloroform having a concentration ratio from about 10:90 to 90:10, by volume; ethanol and dichloromethane having a concentration ratio from about 10:90 to 90:10, by volume; ethanol and chloroform having a concentration ratio from about 10:90 to 90:10, by volume.

In still another embodiment of the present disclosure, the solvent(s) is a mixture selected from a group consisting of methanol and dichloromethane having a concentration ratio of about 10:90 or 20:80 or 30:70, by volume; methanol and chloroform having a concentration ratio of about 10:90 or 20:80 or 30:70, by volume; ethanol and dichloromethane having a concentration ratio of about 10:90 or 20:80 or 30:70, by volume; ethanol and chloroform having a concentration ratio of about 10:90 or 20:80 or 30:70, by volume.

In yet another embodiment of the method described above, the step of crystallizing the product from the solution is carried out by technique selected from a group consisting of controlled linear cooling of IO-125 solution, changing the temperature, anti-solvent addition, evaporation and seeding or any combination thereof.

In still another embodiment of the present disclosure, the anti-solvent is selected from a group consisting of heptane, acetonitrile or any combination thereof.

In still another embodiment of the method described above, said method further comprises isolation of the prepared crystalline Form 1 of compound IO-125.

In still another embodiment of the present disclosure, said isolation of the prepared crystalline Form 1 of compound IO-125 is carried out by acts selected from a group consisting of addition of solvent, distillation, heating, addition of ionic resin, quenching, filtration, extraction, and combinations thereof.

In still another embodiment of the present disclosure, the method as described above is carried out at a temperature ranging from about 0° C. to about 80° C., and for a time period ranging from about one hour to about 48 hours.

In still another embodiment of the present disclosure, the method as described above purifies crude IO-125 to provide a purity of at least 90%, preferably 94% to 97% for the IO-125 compound.

Figure 18:
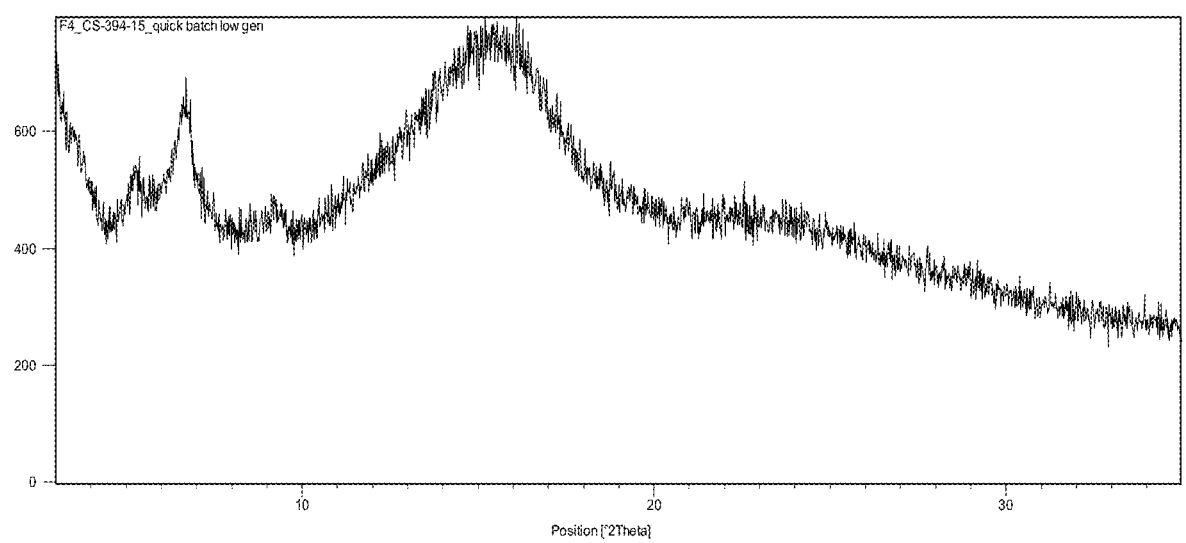
FIG. 18 shows Amorphous IO-125 2θ diffractogram.
Figure 19:
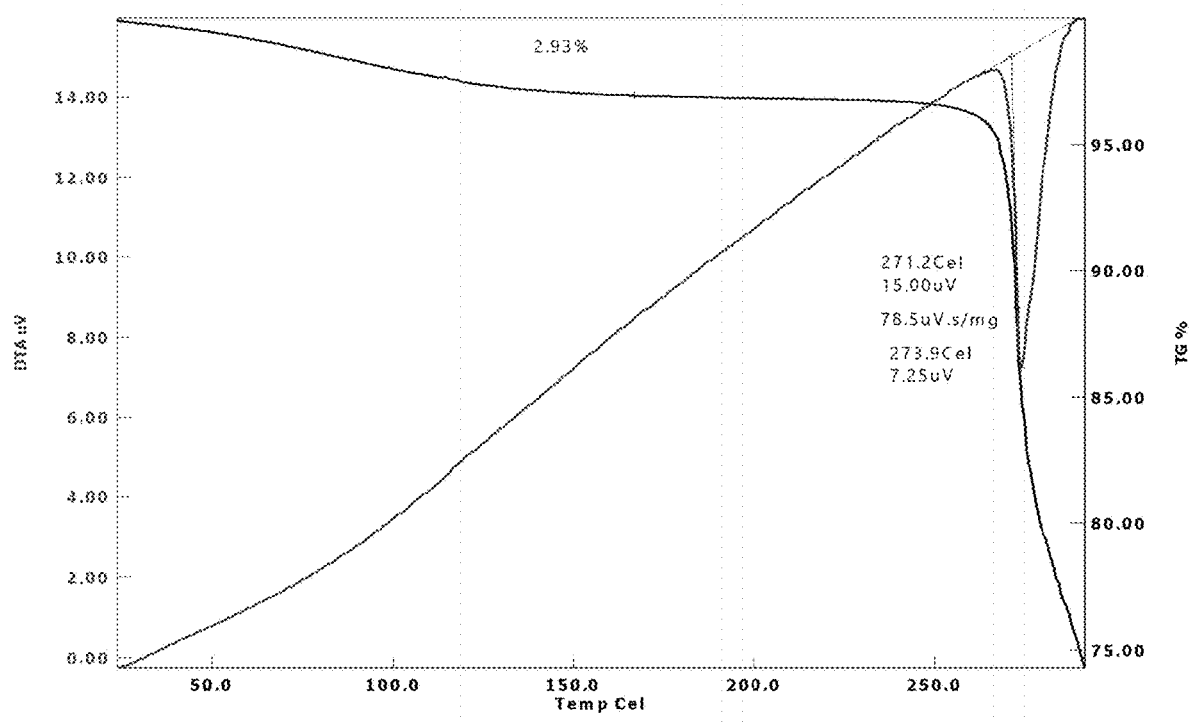
FIG. 19 shows Amorphous IO-125 TG/DTA thermogram (TG trace—blue; DT trace—green).
Figure 20:
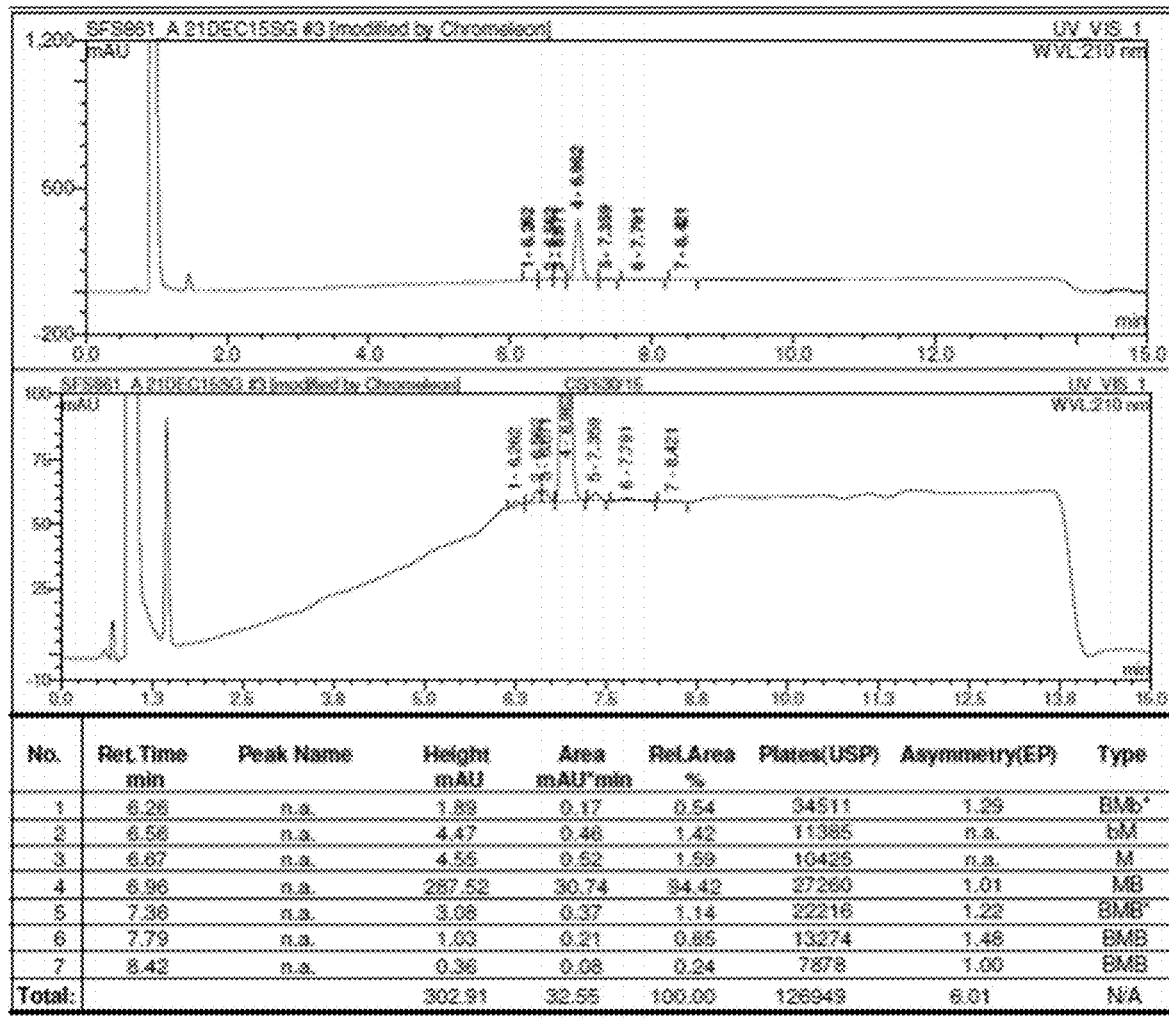
FIG. 20 shows HPLC chromatogram of IO-125, Amorphous.

Initial characterization of the IO-125 was first performed for the purpose of providing a set of reference data. Here, it was found that the material was amorphous with no clear morphology when analyzed by XRPD and PLM respectively. 'Amorphous IO-125' (crude compound) in the present disclosure is further characterised by 2θ diffractogram (FIG. 18), TG/DTA thermogram (FIG. 19) and HPLC chromatogram (FIG. 20). Coupled thermogravimetric/differential thermal analysis (TG/DTA) of IO-125 showed an approximate mass loss of 2.9% (by mass) from measurement start (25° C., ambient conditions), up to approximately 160° C. There were no thermal events observed in the differential thermogram associated with this mass loss. A significant mass loss was then observed in the thermogravimetric trace from approx. 270° C., coupled with a large endothermic event with onset of 271.2° C. and peak at 273.9° C. in the differential thermogram. This is most probably associated with the decomposition of IO-125.

From an initial solubility screen, the IO-125 was found to be mostly insoluble, or very poorly soluble in pure solvents [Table 1]. Solubility was markedly improved in methanol or ethanol:dichloromethane mixtures. Despite this, the screen offered a list of suitable solvents/solvent mixtures and anti-solvents to be used for the crystallization experiments. Using information obtained from the initial investigation into the solubility of IO-125, a series of bench scale crystallization experiments were carried out in order to provide examples of solution-based crystallization method that yield crystalline IO-125. Within this investigation, a number of techniques were designed to find suitable crystallization conditions including: using controlled linear cooling of IO-125 in different solvents, anti-solvent additions, evaporations and seeding. From these experiments, the use of methanol:dichloromethane (20:80% v/v) as the solvent system, with seeding and heptane as the anti-solvent proved to be most promising wherein a crystalline product was returned with no clear morphology by PLM and about 96.61% purity (compared to the crude IO-125 input). By application of these conditions, the impurity peak at approximately 2.50 ppm was found to integrate to 0.15H by 1H NMR (500 MHz, CDCl$_3$:MeOD). TG/DT analysis showed an approximate mass loss of 1.95% (by mass) from measurement start (ambient conditions), up to approx. 250° C. and there were no thermal events observed in the differential thermogram associated with this mass loss. A significant mass loss was then observed in thermogravimetric trace from approx. 270° C., and was coupled with a large endothermic event with onset of 288.4° C. and peak at 297.2° C. in the differential thermogram. Again, this is likely associated with the decomposition of IO-125.

The present disclosure provides a set of example conditions that offer crystalline IO-125 with a purity uplift.

To improve the purity of IO-125, a set of conditions are provided by the present disclosure which result in the crystallisation of compound IO-125 and offer a clear purity uplift. During the present work, a number of amorphous solids were also observed from a variety of solvent systems. PXRD and PLM analysis showed that the solid obtained during some of the crystallization studies were crystalline in nature.

Following protocols are carried out to purify the crude sample of IO-125 and obtain crystalline form:

Protocol 1:

Initially a series of solvents and mixture of solvents were screened to select suitable solvents for the crystallization procedure. As shown in Table 1, mixture of alcohols such as methanol/ethanol and chloroform/dichloromethane are suitable solvent mixtures for the crystallization procedure.

TABLE 1

Summary of Comp 25 solubility data in pure solvents and mixtures

| Solvent/Solvent Mixtures | Approximate Solubility | XRPD Analysis on material after temperature cycling |
| --- | --- | --- |
| 1,4-dioxane | ≤10 mg/ml | |
| 1-Butanol | ≤10 mg/ml | |
| 1-Propanol | 20 mg/ml | |
| 2-Butanol | ≤10 mg/ml | Amorphous |
| 2-Mehyl Ethanol | ≤10 mg/ml | |
| 2-Methyl THF | ≤10 mg/ml | Amorphous |
| Acetone | ≤10 mg/ml | |
| Acetonitrile | ≤10 mg/ml | Amorphous |
| Anisole | ≤10 mg/ml | Amorphous |
| Chloroform | ≤133 mg/ml | Crystalline |
| Dichloromethane | ≤15 mg/ml | |
| Dimethylacetamide | ≤10 mg/ml | Amorphous |
| Dimethylformamide | ≤10 mg/ml | Amorphous |
| Dimethylsulfoxide | ≤10 mg/ml | |
| Ethanol (absolute) | ≤15 mg/ml | |
| Ethyl Acetate | ≤10 mg/ml | Amorphous |
| Ethylene Glycol | ≤10 mg/ml | |
| Heptane | ≤10 mg/ml | |
| Propan-2-ol | ≤10 mg/ml | |
| Methanol | ≤10 mg/ml | |
| Tert-butyl Methyl ether | ≤10 mg/ml | Amorphous |
| Tetrahydrofuran | ≤10 mg/ml | |
| Toluene | ≤10 mg/ml | Amorphous |
| Water | ≤10 mg/ml | Amorphous |
| Methanol:Chloroform (50:50 v/v %) | ≤200 mg/ml | Crystalline |
| Methanol:Dichloromethane (50:50 v/v %) | ≤200 mg/ml | Crystalline |
| Ethanol:Chloroform (50:50 v/v %) | ≤200 mg/ml | Crystalline |
| Ethanol:Dichloromethane (50:50 v/v %) | ≤200 mg/ml | Crystalline |
| Methanol:Dichloromethane (90:10 v/v %) | ≤66 mg/ml | Crystalline |
| Ethanol:Dichloromethane (90:10 v/v %) | ≤66 mg/ml | Crystalline |
| Methanol:Dichloromethane (80:20 v/v %) | ≤200 mg/ml | Crystalline |
| Methanol:Dichloromethane (70:30 v/v %) | ≤200 mg/ml | Crystalline |
| Methanol:Dichloromethane (60:40 v/v %) | ≤200 mg/ml | Crystalline |
| Methanol:Dichloromethane (40:60 v/v %) | ≤200 mg/ml | Crystalline |
| Methanol:Dichloromethane (30:70 v/v %) | ≤200 mg/ml | Crystalline |
| Methanol:Dichloromethane (20:80 v/v %) | ≤200 mg/ml | Crystalline |
| Methanol:Dichloromethane (10:90 v/v %) | ≤200 mg/ml | Crystalline |
| Ethanol:Dichloromethane (80:20 v/v %) | ≤80 mg/ml | |
| Ethanol:Dichloromethane (70:30 v/v %) | ≤200 mg/ml | Amorphous |
| Ethanol:Dichloromethane (60:40 v/v %) | ≤200 mg/ml | Amorphous |
| Ethanol:Dichloromethane (40:60 v/v %) | ≤200 mg/ml | Crystalline |
| Ethanol:Dichloromethane (30:70 v/v %) | ≤200 mg/ml | Crystalline |
| Ethanol:Dichloromethane (20:80 v/v %) | ≤200 mg/ml | Crystalline |
| Ethanol:Dichloromethane (10:90 v/v %) | ≤200 mg/ml | Crystalline |

Protocol 2:

In an embodiment of the present disclosure, the method for preparing crystalline Form 1 of compound IO-125 comprises:

(i) preparing a solution of IO-125 by dissolving crude IO-125 in a mixture of lower alkyl alcohol and halogenated hydrocarbon solvent system; and (ii) crystallizing product from the solution by temperature cycling.

Figure 1:
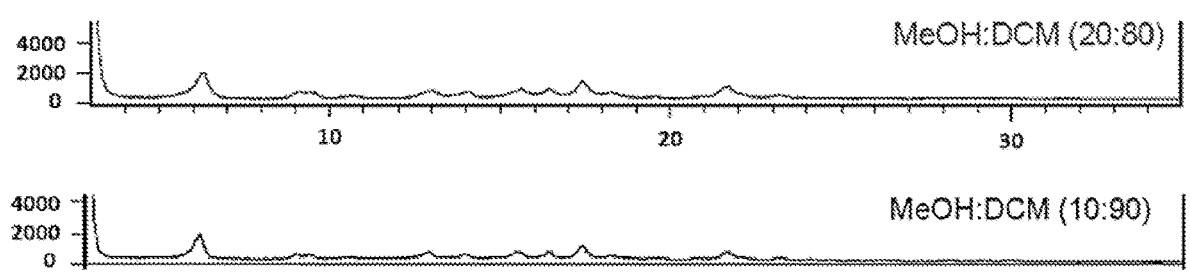
FIG. 1 shows XRPD 2θ diffractograms of solids recovered from successful crystallisation screening of crude COMP 25 obtained by way of protocol 2.

Crystallisation Screening on Crude Compound 25 on Selected Solvents:

Crystallisation screening on crude compound 25 (COMP 25) was carried out using Methanol:Dichloromethane and Ethanol:Dichloromethane solvent mixtures. The material isolated from each experiment after temperature cycling was analysed by XRPD and the results are summarized in Table 2. Crystalline COMP 25 was obtained using methanol:dichloromethane (20:80% v/v) and (10:90% v/v) solvent systems. All other methanol:dichloromethane and ethanol:dichloromethane solvent mixtures produced amorphous material. XRPD 2θ diffractograms of solids recovered from successful crystallisation screening of crude COMP 25 are shown in FIG. 1.

TABLE 2

Crystallization Screening on Crude COMP 25

| Solvent System (% v/v) | Isolated material |
| --- | --- |
| Methanol:Dichloromethane (90:10) | Amorphous |
| Methanol:Dichloromethane (80:20) | Amorphous |
| Methanol:Dichloromethane (70:30) | Amorphous |
| Methanol:Dichloromethane (60:40) | Amorphous |
| Methanol:Dichloromethane (50:50) | Amorphous |
| Methanol:Dichloromethane (40:60) | Amorphous |
| Methanol:Dichloromethane (30:70) | Amorphous |
| Methanol:Dichloromethane (20:80) | Crystalline |
| Methanol:Dichloromethane (10:90) | Crystalline |
| Ethanol:Dichloromethane (90:10) | Amorphous |
| Ethanol:Dichloromethane (80:20) | Amorphous |
| Ethanol:Dichloromethane (70:30) | Amorphous |
| Ethanol:Dichloromethane (60:40) | Amorphous |
| Ethanol:Dichloromethane (50:50) | Amorphous |
| Ethanol:Dichloromethane (40:60) | Amorphous |
| Ethanol:Dichloromethane (30:70) | Amorphous |
| Ethanol:Dichloromethane (20:80) | Amorphous |
| Ethanol:Dichloromethane (10:90) | Amorphous |

Protocol 3:

In another embodiment of the present disclosure, the method for preparing a crystalline Form 1 of compound IO-125 comprises:

(i) preparing a solution of IO-125 by dissolving crude IO-125 in a mixture of lower alkyl alcohol and halogenated hydrocarbon solvent system; and (ii) crystallizing product from the solution by adding a seed of crystalline IO-125 to the solution followed by heating and cooling.

Seeded Cooling Crystallization of Crude COMP 25—General Procedure:

Approximately 20 mg of Crude COMP 25 was weighed into a 2 ml glass vial and 100 NL of respective solvent system was added to the experiments at ca. about 25° C. All solvents were dried over pre-dried 3 A molecular sieves (where appropriate) prior to use. A small (approx. 1 mg) amount of crystalline COMP 25 was added as a seed to the experiments. The experiments were heated to about 40° C. The experiments were cooled down to about 5° C. at ca. 0.11° C./minute. The experiments were stirred at about 5° C. for about 3 hours and temperature cycled between 5° C. to 40° C. at about 0.2° C./minute overnight (ca. 18 hours). The experiments where solid material was observed, the solids were isolated using centrifuge at ambient (ca. 22° C.) and analysed by XRPD. Table 3 summarizes the solvent systems used for seeded, cooling crystallisation of crude COMP 25.

TABLE 3

Solvent systems used for seeded, cooling crystallization of crude COMP 25

| Solvent System | (% v/v) |
|---|---|
| Methanol:Dichloromethane | (30:70) |
| Methanol:Dichloromethane | (20:80) |
| Methanol:Dichloromethane | (10:90) |
| Ethanol:Dichloromethane | (30:70) |
| Ethanol:Dichloromethane | (20:80) |
| Ethanol:Dichloromethane | (10:90) |

Figure 2:
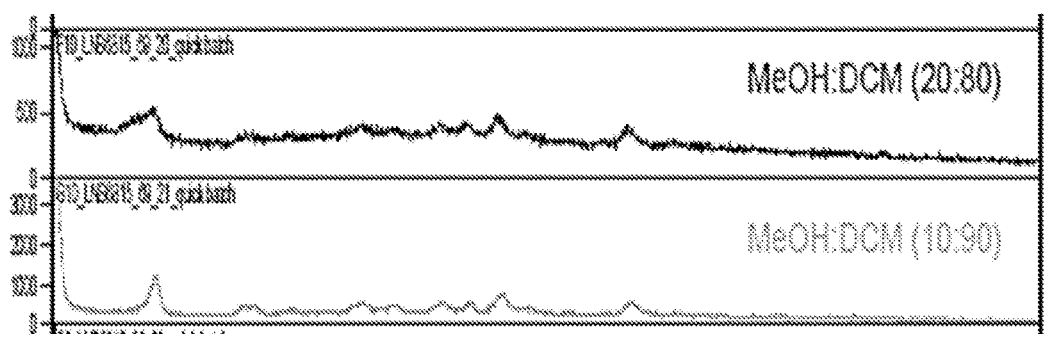
FIG. 2 shows XRPD 2θ diffractograms on solids after temperature cycling obtained by way of protocol 3.
Figure 3:
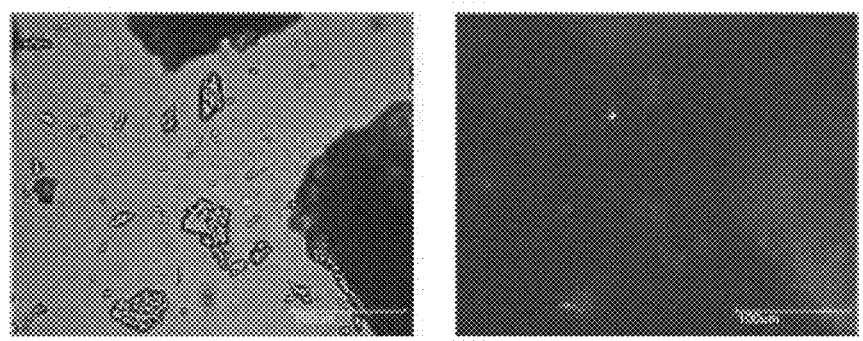
FIG. 3 shows PLM micrographs of crystalline material obtained from seeded methanol:dichloromethane (10:90% v/v) obtained by way of protocol 3.

The experimental conditions that returned the reoccurring crystalline form was methanol:dichloromethane (10:90% v/v). Methanol:dichloromethane (20:90% v/v) returned weakly crystalline material. All Ethanol:Dichloromethane mixtures and methanol:dichloromethane (30:70% v/v) returned amorphous material. FIG. 2 shows XRPD 2θ diffractograms on solids after temperature cycling and FIG. 3 shows PLM micrographs of crystalline material obtained from seeded methanol:dichloromethane (10:90% v/v).

Protocol 4:

In yet another embodiment of the present disclosure, the method for preparing a crystalline Form 1 of compound IO-125 comprises
 (i) preparing a solution of IO-125 by dissolving crude IO-125 in a mixture of lower alkyl alcohol and halogenated hydrocarbon solvent system; and
 (ii) crystallizing the product from the solution by cooling and temperature cycling.

Figure 4:
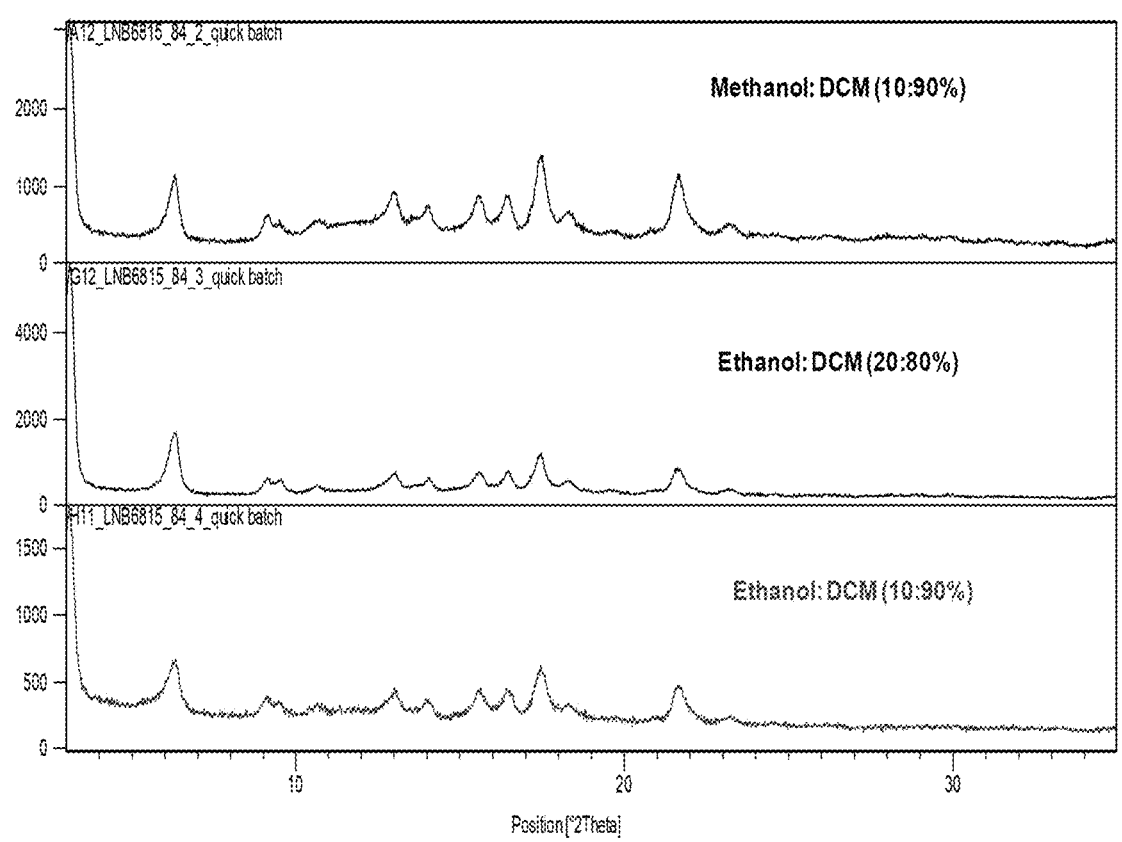
FIG. 4 shows XRPD 2θ diffractograms of exemplary solids after temperature cycling at concentration ca. 150 mg/ml obtained by way of protocol 4.

Cooling Crystallization of Crude COMP 25 (20 mg Trial)—General Procedure:

Crude COMP 25 was weighed into a 2 mL sample vial and a known aliquot of solvent added at ca. 25° C. The mixture was stirred at about 25° C. The mixture was cooled down from about 25° C. to about 5° C. at ca. 0.11° C./minute. The mixture was again stirred at about 5° C. for about 3 hours. The temperature cycled between about 5° C. to 40° C. at ca. 0.2° C./minutes. The experiments where solid material was observed, the solids were isolated at about 25° C. using centrifuge and analysed by XRPD. Table 4 summarizes the conditions used for cooling crystallization and Table 5 summarizes the conditions for cooling crystallisation in double scale. Tables 6 and 7 summarize the results and observations for the cooling crystallization studies. XRPD 2θ diffractograms of exemplary solids after temperature cycling at concentration ca. 150 mg/ml are shown in FIG. 4.

TABLE 4

Conditions for cooling crystallization

| Solvent system (% v/v) | Volume of Solvent (μL) | Mass of crude IO-125 (mg) | Concentration (mg/mL) |
|---|---|---|---|
| Methanol:Dichloromethane (40:60) | 150 | 20.49 | 136.6 |
| Methanol:Dichloromethane (30:70) | 150 | 18.69 | 124.6 |
| Methanol:Dichloromethane (20:80) | 150 | 20.31 | 135.4 |
| Methanol:Dichloromethane (10:90) | 150 | 20.23 | 134.87 |
| Ethanol:Dichloromethane (40:60) | 150 | 20.56 | 137.07 |
| Ethanol:Dichloromethane (30:70) | 150 | 20.33 | 135.53 |
| Ethanol:Dichloromethane (20:80) | 150 | 19.46 | 129.73 |
| Ethanol:Dichloromethane (10:90) | 150 | 19.51 | 130.07 |

TABLE 5

Conditions for cooling crystallisation in double scale

| Solvent system (% v/v) | Volume of Solvent (μL) | Mass of crude IO-125 (mg) | Concentration (mg/mL) |
|---|---|---|---|
| Methanol:Dichloromethane (20:80) | 333 | 49.38 | 148.29 |
| Methanol:Dichloromethane (10:90) | 333 | 50.13 | 150.54 |
| Ethanol:Dichloromethane (20:80) | 333 | 50.73 | 152.34 |
| Ethanol:Dichloromethane (10:90) | 333 | 49.84 | 149.67 |

TABLE 6

Summary of results and observations for the cooling crystallizations

| Solvent system (% v/v) | Concentration (mg/mL) | Observations After temperature cycling | XRPD Analysis Results |
|---|---|---|---|
| Methanol:Dichloromethane (40:60%) | 136.6 | Clear Solution, No precipitation | No Precipitation |
| Methanol:Dichloromethane (30:70%) | 124.6 | Clear Solution, No precipitation | No Precipitation |
| Methanol:Dichloromethane (20:80%) | 135.4 | Clear Solution, No precipitation | No Precipitation |
| Methanol:Dichloromethane (10:90%) | 134.87 | White Slurry | Crystalline |
| Ethanol:Dichloromethane (40:60%) | 137.07 | Clear Solution, No precipitation | No Precipitation |
| Ethanol:Dichloromethane (30:70%) | 135.53 | Clear Solution, No precipitation | No Precipitation |
| Ethanol:Dichloromethane (20:80%) | 129.73 | White Solid | Crystalline |
| Ethanol:Dichloromethane (10:90%) | 130.07 | White Solid | Crystalline |

TABLE 7

Summary of results and observations for the cooling crystallizations

| Solvent system (% v/v) | Concentration (mg/mL) | Observations After temperature cycling | XRPD Analysis Results |
|---|---|---|---|
| Methanol:Dichloromethane (20:80%) | 148.29 | Clear Solution, No precipitation | No Precipitation |
| Methanol:Dichloromethane (10:90%) | 150.54 | White Slurry | Crystalline |
| Ethanol:Dichloromethane (20:80%) | 152.34 | White Solid | Crystalline |
| Ethanol:Dichloromethane (10:90%) | 149.67 | White Solid | Crystalline |

Protocol 5:

In still another embodiment of the present disclosure, the method for preparing a crystalline Form 1 of compound IO-125 comprises:
(i) preparing a solution of IO-125 by dissolving crude IO-125 in a mixture of lower alkyl alcohol and halogenated hydrocarbon solvent system;
(ii) crystallizing the product from the solution by adding anti-solvent to the solution followed by cooling and temperature cycling; and
(iii) optionally repeating step (ii).

Figure 5:
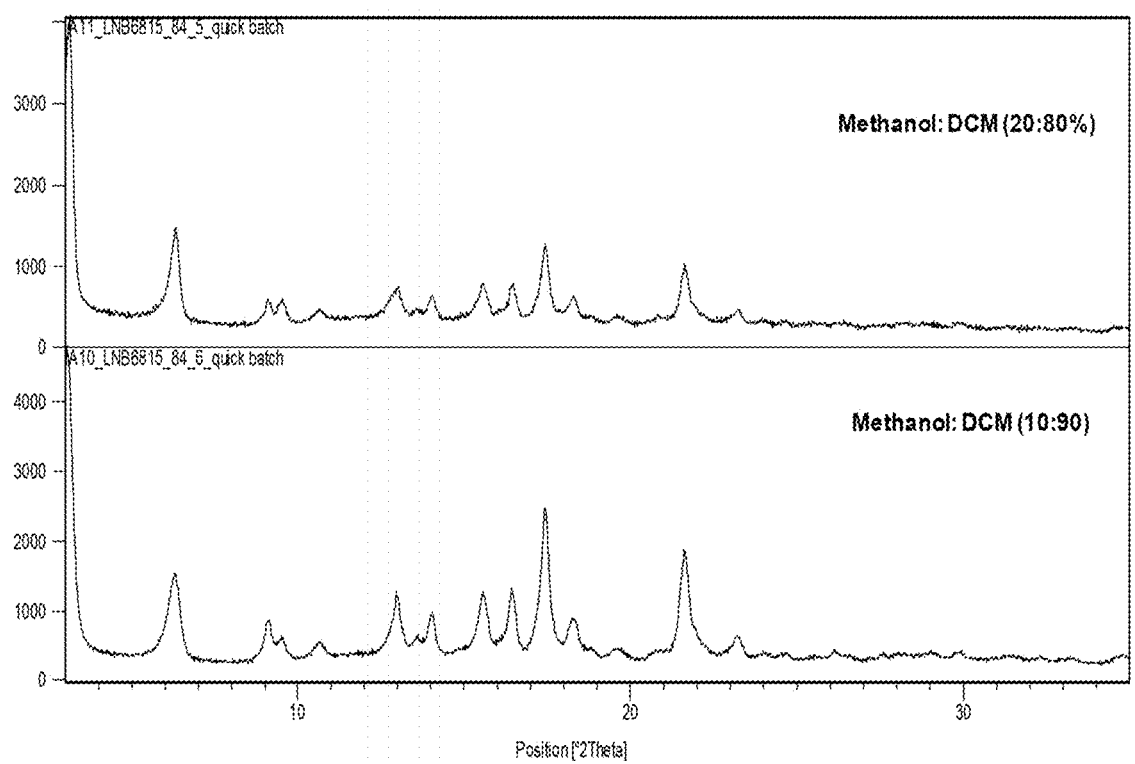
FIGS. 5 and 6 show XRPD 2θ diffractograms of solids after temperature cycling, anti-solvent used heptanes obtained by way of protocol 5.
Figure 6:
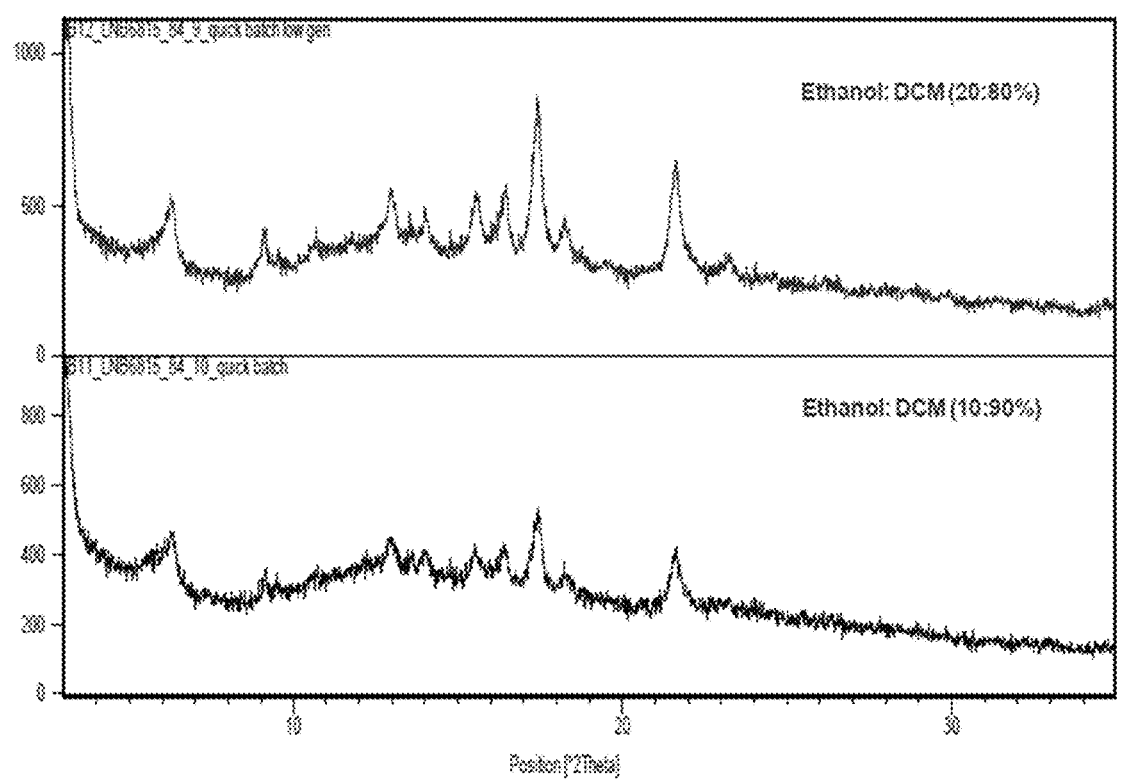

Anti-Solvent/Cooling Crystallization of Crude COMP 25—General Procedure:

Approximately 50 mg COMP 25 Crude was weighed into a 2 mL sample vial and appropriate volume of respective solvent was added at ca. 25° C. Respective anti-solvent was added to appropriate vial in 25 microL aliquots at ca. 25° C. The experiments were cooled down from about 25° C. to 5° C. at ca. 0.11° C./minute. The mixture was stirred at about 5° C. for about 3 hours. The experiments were temperature cycled between about 5° C. to 40° C. at ca. 0.2° C./minute overnight (ca. 18 hours). The experiments where thin slurry or clear solution were observed, further anti-solvent was added to the experiments at ca. 25° C. The experiments were cooled down from about 25° C. to 5° C. at ca. 0.11° C./minute, and stirred at about 5° C. for about 3 hours. The experiments were temperature cycled overnight between about 5° C. to 40° C. at ca. 0.2° C./minute overnight (ca. 18 hours). The experiments where solid material was observed, the solids were isolated at ambient (ca. 22° C.) using centrifuge and analysed by XRPD. Samples that were isolated were then dried under vacuum at ambient temperature overnight. Using 2-methyl THF as an anti-solvent, the crystallisations were resulted in formation of gel like material using methanol:dichloromethane solvent mixtures and ethanol:dichloromethane (30:70% v/v) solvent system. Using heptane as an anti-solvent crystalline material was observed using most of the solvent systems. As shown in Tables 8 and 9, using acetonitrile as an anti-solvent, partially crystalline material was observed using most of the solvent systems. XRPD 2θ diffractograms of solids after temperature cycling, anti-solvent used heptanes are shown in FIGS. 5 and 6.

TABLE 8

Observations and results for anti-solvent addition/cooling crystallizations

| Solvent system (% v/v) | Anti-solvent | Concentration (mg/mL) | Observations | Observations after overnight temperature cycling | Observations after further temperature cycling | XRPD Analysis Results |
|---|---|---|---|---|---|---|
| Methanol:Dichloromethane (30:70%) | Heptane | 189.8 | Clear Solution | White Slurry | Slurry | Crystalline |
| Methanol:Dichloromethane (20:80%) | | 192.2 | Clear Solution | Thick White Slurry | Thick slurry | Crystalline |
| Methanol:Dichloromethane (10:90%) | | 202.3 | Clear Solution | Thick White Slurry | Thick slurry | Crystalline |
| Methanol:Dichloromethane (30:70%) | Acetonitrile | 109.14 | Thick precipitation, further 75 μL of solvent system added to make thin slurry | Some Precipitation | Slurry | Partially crystalline |
| Methanol:Dichloromethane (20:80%) | | 110.74 | Thick precipitation, further 75 μL of solvent system added to make thin slurry | Some Precipitation | Slurry | Partially crystalline |
| Methanol:Dichloromethane (10:90%) | | 104.55 | Thick precipitation, further 75 μL of solvent system added to make thin slurry | Some Precipitation | Slurry | Partially crystalline |
| Methanol:Dichloromethane (30:70%) | 2-methyl THF | 202.1 | Clear Solution | Clear Solution, No precipitation | Gel like | N/A |
| Methanol:Dichloromethane (20:80%) | | 212.8 | Clear Solution | Clear Solution, No precipitation | Gel like | N/A |
| Methanol:Dichloromethane (10:90%) | | 205.8 | Clear Solution | Thick clear gel | Gel like | N/A |

TABLE 9

Observations and results for anti-solvent addition/cooling crystallizations

| Solvent system (% v/v) | Anti-solvent | Concentration (mg/mL) | Observations | Observations after overnight temperature cycling | Observations after further temperature cycling | XRPD Analysis Results |
|---|---|---|---|---|---|---|
| Ethanol:Dichloromethane (30:70%) | Heptane | 190.8 | Clear Solution | White Slurry | Slurry | Crystalline |
| Ethanol:Dichloromethane (20:80%) | | 200.8 | Clear Solution | Thick White Slurry | Slurry | Crystalline |
| Ethanol:Dichloromethane (10:90%) | | 211.9 | Clear Solution | Clear Gel | Gel | N/A |
| Ethanol:Dichloromethane (30:70%) | Acetonitrile | 141.33 | Thick precipitation | Some Precipitation | Slurry | Partially crystalline |
| Ethanol:Dichloromethane (20:80%) | | 139.33 | Thick precipitation | White Slurry | Slurry | Partially crystalline |
| Ethanol:Dichloromethane (10:90%) | | 108 | Thick precipitation | White Gum | Slurry | Partially crystalline |
| Ethanol:Dichloromethane (30:70%) | 2-methyl THF | 196 | Clear Solution | Gel like | Gel like | N/A |

Figure 7:
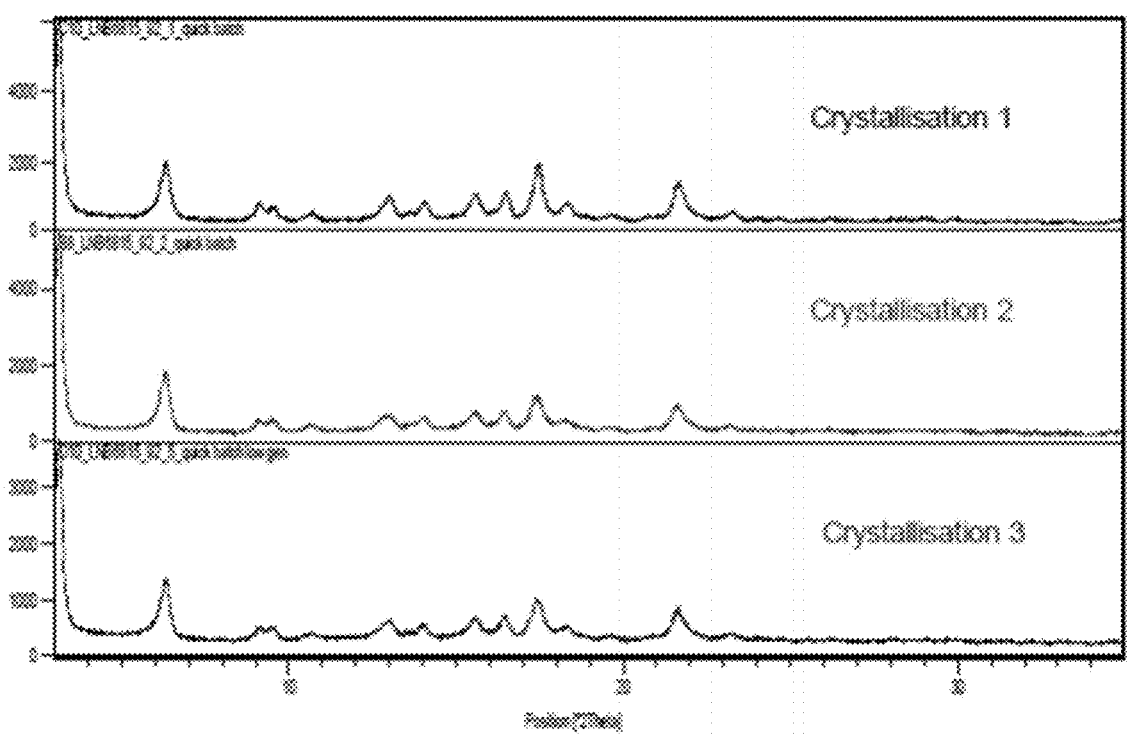
FIGS. 7 and 8 show XRPD 2θ diffractograms and PLM of solids obtained by way of protocol 6.
Figure 8:
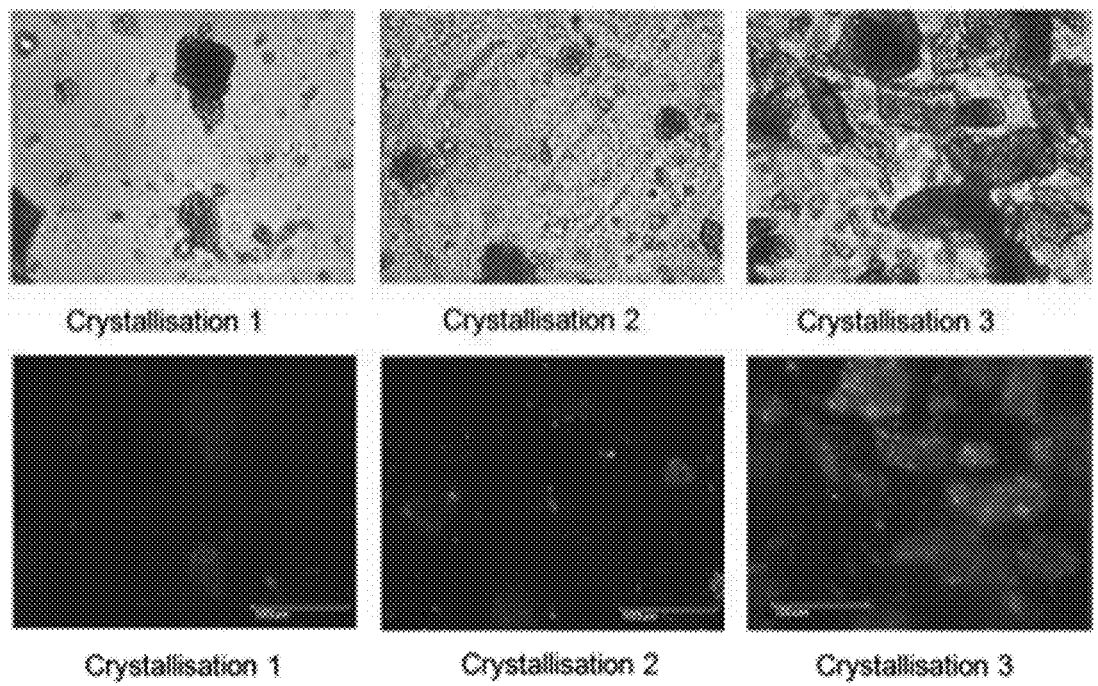
Figure 9:
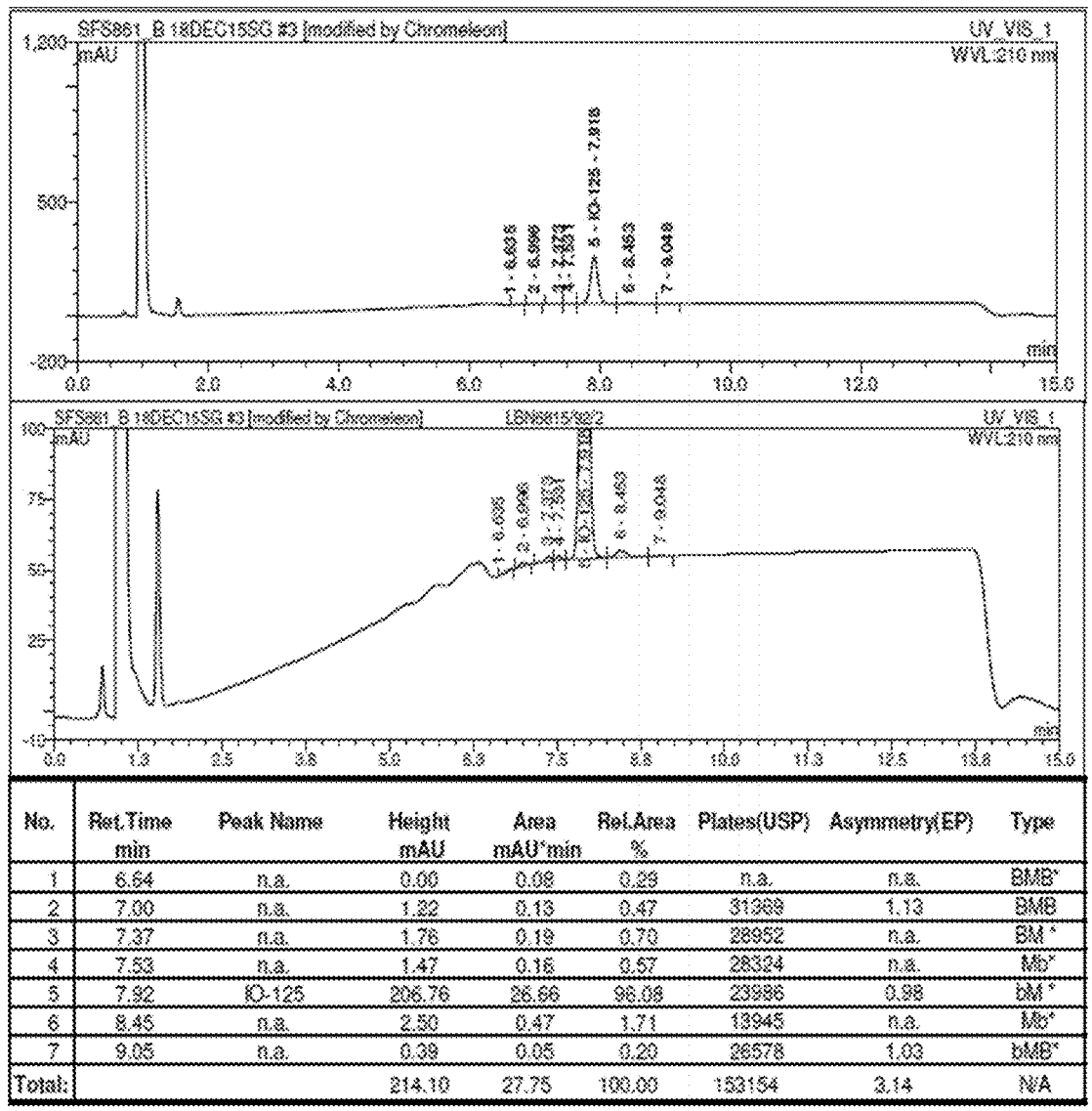
FIG. 9 shows HPLC chromatogram of solids of an exemplary cooling crystallization 2 obtained by way of protocol 6.

Protocol 6:

Cooling Crystallization of Crude COMP 25 (200-250 mg Scale) General Procedure:

Respective mass of COMP 25 Crude was weighed into a 20 mL sample vial and appropriate volume of respective solvent system was added at ca. 25° C. to dissolve the sample. The experiments were cooled down to about] 5° C. at ca. 0.1° C./min, stirred at about 5° C. for about 2 hours followed by temperature cycling between about 5° C. to 40° C. The experiments were thereafter heated to about 40° C. over about 2 hours (ca. 0.3° C./minute). The mixture was again stirred at about 40° C. for about 2 hours, cooled down to about 5° C. over about 2 hours (ca. 0.3° C./minute), followed by stirred at about 5° C. for about 2 hours. Samples were isolated at ambient (ca. 22° C.) by filtering over Buchner funnel under vacuum using Whatmann filter paper No. 1, then dried under vacuum at ambient temperature overnight (approx. 18 hours). The solid material was then analysed by XRPD and PLM. Results are summarized in Table 10 and shown in FIGS. 7 and 8. HPLC chromatogram of an exemplary cooling crystallization 2 is shown in FIG. 9.

TABLE 10

Observations and Results for cooling crystallization

| Solvent system (% v/v) | Concentration (mg/mL) | XRPD analysis | Isolated yield | HPLC purity | Crystallisation number |
|---|---|---|---|---|---|
| Methanol:Dichloromethane (20:80) | 250 | Crystalline | 30% | 93.98% | 1 |
| Methanol:Dichloromethane (10:90) | 250 | Crystalline | 51% | 96.08% | 2 |
| Methanol:Dichloromethane (10:90) | 250 | Crystalline | 20% | 95.04% | 3 |

Protocol 7:

Seeded Cooling Crystallization of Crude COMP 25 (250 mg Scale)—General Procedure:

Respective mass of Crude COMP 25 was weighed into a 20 mL sample vial and appropriate volume of respective solvent system was added at ca. 25° C. to dissolve the sample. Crystalline COMP 25 was added to the experiments as a seed. The experiments were cooled down to about 5° C. at ca. 0.1° C./min, stirred at about 5° C. for about 2 hours, temperature cycled between about 5° C. to 40° C., heated to about 40° C. over about 2 hours (ca. 0.3° C./minute). The experiments were thereafter stirred at about 40° C. for about 2 hours, cooled down to about 5° C. over about 2 hours (ca. 0.3° C./minute) And stirred at about 5° C. for about 2 hours. The samples were isolated at ambient (ca. 22° C.) by filtering over Buchner funnel under vacuum using Whatmann filter paper No. 1, then dried under vacuum at ambient temperature overnight (ca. 18 hours). The solid material was then analysed by XRPD and PLM. Results are summarized in Table 11 and shown in FIGS. 10 and 11.

Figure 12:
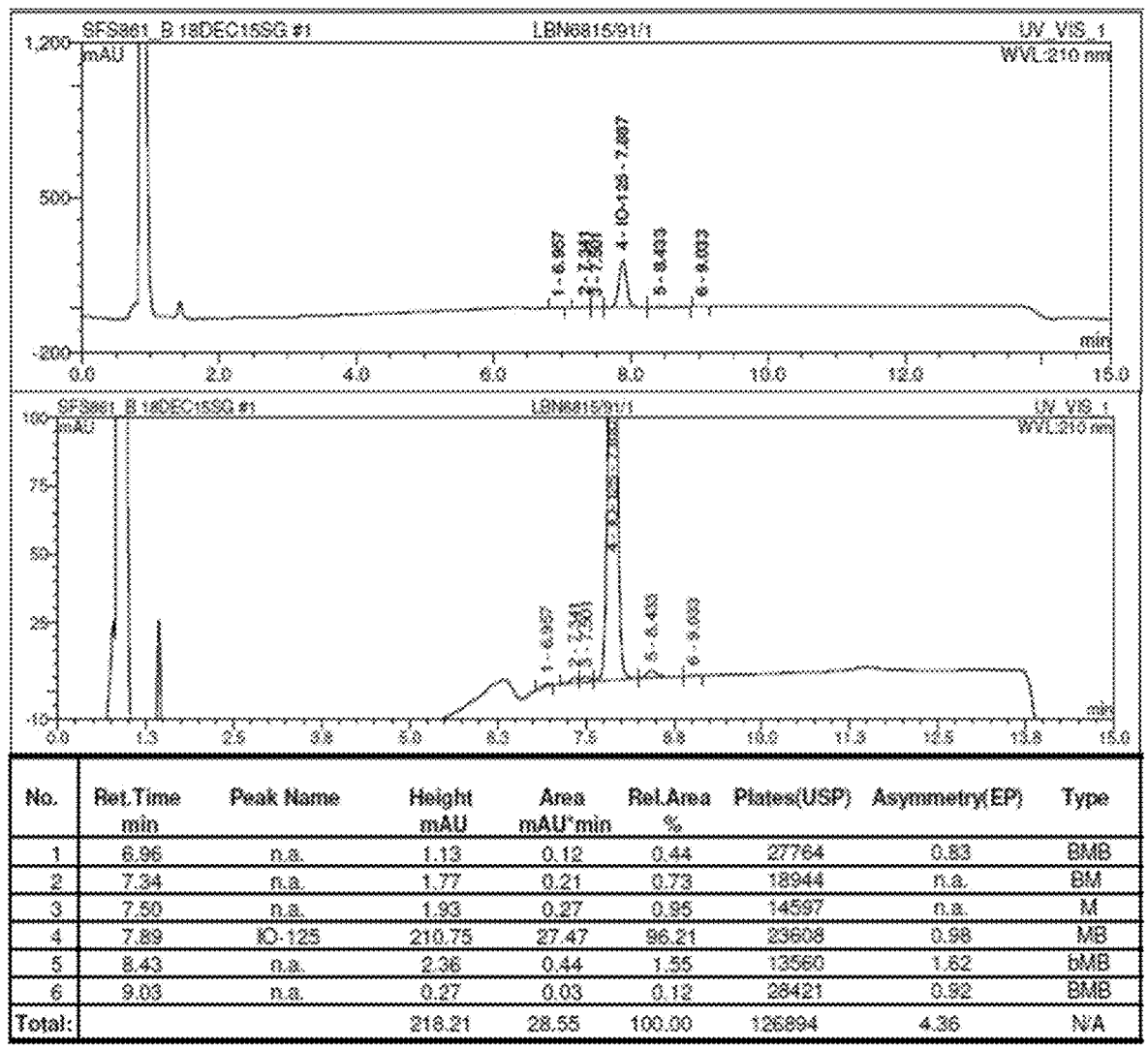
FIG. 12 shows HPLC chromatogram of solids obtained by way of protocol 7.

Solvent mixture methanol:dichloromethane (10:90% v/v) at a concentration of 160 mg/ml was employed wherein the material returned was crystalline and had a purity of at least 96.65% by HPLC. The calculated yield for this experiment was about 36%. Further, when solvent mixture methanol:dichloromethane (20:80% v/v) was employed at a concentration of 190 mg/ml, the material returned was crystalline and had a purity of at least 96.21% by HPLC (FIG. 12). The calculated yield for this experiment was about 41%.

TABLE 11

Conditions for seeded cooling crystallization

| Solvent system (% v/v) | Input (mg) | solvent (mL) | Concentration (mg/mL) |
|---|---|---|---|
| Methanol:Dichloromethane (20:80) | 254.01 | 1.32 | 190.00 |
| Methanol:Dichloromethane (10:90) | 250.08 | 1.56 | 160.00 |

Protocol 8:

In still another embodiment of the present disclosure, the method for preparing a crystalline Form 1 of compound IO-125, comprising
  (i) preparing a solution of IO-125 by dissolving crude IO-125 in a mixture of lower alkyl alcohol and halogenated hydrocarbon solvent system; and
  (ii) crystallizing the product from the solution by adding anti-solvent and a seed of crystalline IO-125 to the solution, and, cooling and temperature cycling followed by heating and cooling.

Figure 13:
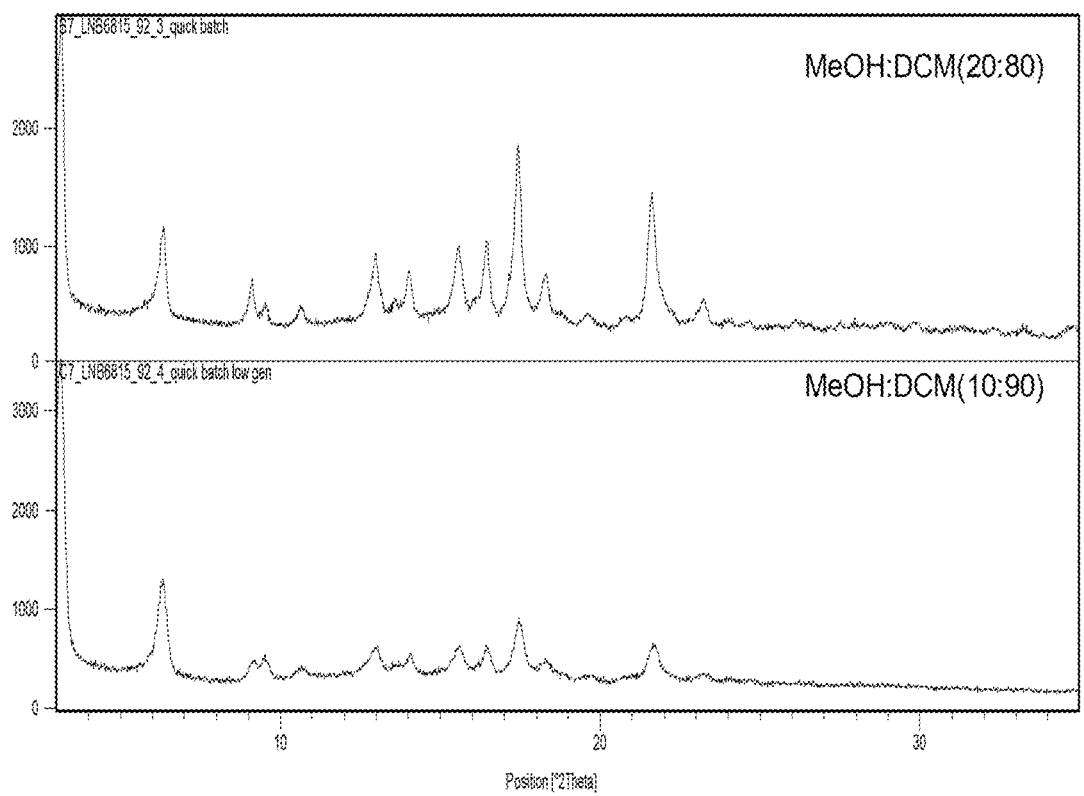
FIGS. 13 and 14 show XRPD 2θ diffractograms and PLM of solids obtained by way of protocol 8.
Figure 14:
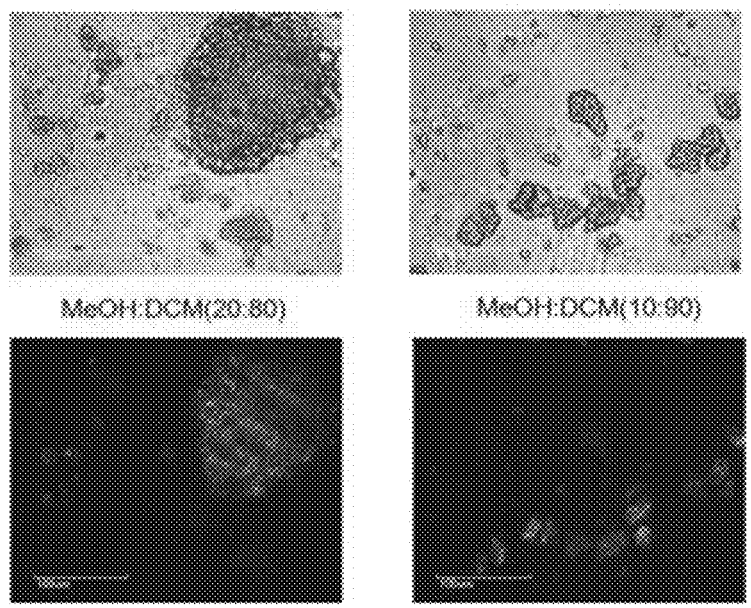

Seeded, Anti-Solvent and Cooling Crystallization General Procedure:

Approximately 250 mg Crude COMP 25 was weighed into a 20 mL sample vial and appropriate volume of respective solvent system was added at ca. 25° to dissolve the IO-125. Heptane was added as an anti-solvent in 250 microL aliquots. Total 1 ml heptane was added to each experiment. The experiments were seeded using crystalline COMP 25 (approx. 5 mg). The experiments were stirred at about 25° C. for ca. 1 hour and then cooled down to about 5° C. at ca. 0.1° C./minute. The samples were stirred at about 5° C. for about 2 hours, temperature cycled between about 5° C. to 40° C. Heated to about 40° C. over about 2 hours (ca. 0.3° C./minute), Followed by stirring at about 40° C. for about 2 hours, cooling down to about 5° C. over about 2 hours (ca. 0.3° C./minute) And stirred again at about 5° C. for about 2 hours. The experiments were isolated at ambient (ca. 22° C.) by filtering over Buchner funnel under vacuum using Whatmann filter paper no 1 and then dried under vacuum at ambient temperature overnight (ca. 18 hours). The solid material was then analysed by XRPD (FIG. 13) and PLM (FIG. 14). The combination of all three techniques was used to see if there was any difference in the material produced from solvent systems and also to see if the best crystallisation conditions have been found. Yield calculations were carried out and are summarized in Table 12. HPLC chromatogram of an isolated solid using methanol:dichloromethane (20:80% v/v) with heptanes as anti-solvent is shown in FIG. 15.

TABLE 12

Experimental observation of seeded, anti-solvent and cooling crystallization

| Solvent system (% v/v) | Concentration (mg/mL) | Anti-solvent | Concentration (mg/mL) | XRPD Analysis | Yield | HPLC Purity |
|---|---|---|---|---|---|---|
| Methanol:Dichloromethane (20:80) | 333 | Heptane | 142.86 | Crystalline | 48% | 96.61% |
| Methanol:Dichloromethane (10:90) | 333 | Heptane | 142.86 | Crystalline | 51% | 96.35% |

Protocol 9:
Crystallization Using Organic Acid and Halogenated Hydrocarbon Solvent:

About 38.0 g crude dried IO-125 was charged with about 4 w/w water. After stirring for 1.5 hours at about 70° C., cooling, and addition of about 16 w/w acetone, about 35.8 g crystallized IO-125 was isolated by filtration and washing is carried out with about 1 w/w water. The slurry is repeated once again delivering about 34.4 g crude dried product after drying under vacuum at about 50° C. This was in turn dissolved in about 26.5 w/w dichloromethane and about 1 w/w acetic acid and the solution filtered (polish).

After addition of about 10 w/w ethanol and distillation to about 8.6 v/w, the crystallized wet product (about 32.3 g) is isolated by filtration and washed with about 1 w/w ethanol. Drying is performed in vacuum at about 40° C. which afforded about 21.8 g of crystallised dried product. IPC showed about 1.68% w/w of acetic acid. In order to reduce its amount, an additional slurry was performed on about 17.8 g, delivering about 16.3 g of material with about 0.23% acetic acid content. The value reported in the analytical results table 13 is n. d. (not detected) because another slurry is performed due to an analytical issue which at first erroneously resulted in a higher acetic acid content.

The present disclosure relates to a method for preparing crystalline Form 1 of compound IO-125, comprising
  (i) preparing a solution of IO-125 by dissolving crude IO-125 in an organic acid and a halogenated hydrocarbon solvent mixture;
  (ii) adding lower alkyl alcohol to the solution to obtain a solution 2; and
  (iii) crystallizing the product from said solution 2.

In an embodiment of the present disclosure, the organic acid is acetic acid, halogenated hydrocarbon solvent is dichloromethane and the lower alkyl alcohol is ethanol.

In another embodiment of the present disclosure, the concentration ratio of acetic acid to dichloromethane is about 0.5-1: 25-30, by weight, preferably about 1:26.5, by weight.

In yet another embodiment of the present disclosure, the step of crystallizing the product is carried out by technique selected from a group consisting of controlled linear cooling of IO-125 solution, changing the temperature, anti-solvent addition, evaporation and seeding, or any combination thereof.

In still another embodiment of the present disclosure, the anti-solvent is selected from a group consisting of heptane, acetonitrile, and combination thereof.

In still another embodiment of the present disclosure, the method for preparing crystalline Form 1 of compound IO-125 comprises:
  (i) preparing a solution of IO-125 by dissolving crude IO-125 in acetic acid and dichloromethane mixture;
  (ii) adding ethanol to the solution to obtain a solution 2; and
  (iii) crystallizing the product from the said solution 2 by cooling.

In still another embodiment of the present disclosure, the method further comprises isolation of the prepared crystalline Form 1 of compound IO-125.

In still another embodiment of the present disclosure, the isolation is carried out by acts selected from a group consisting of addition of solvent, distillation, heating, addition of ionic resin, quenching, filtration, extraction, and combinations thereof.

In still another embodiment of the present disclosure, the method is carried out at a temperature ranging from about 0° C. to about 80° C., linear cooling is carried out to 5° C. at a rate of 0.11° C./min, and for a time period ranging from about one hour to about 48 hours.

In still another embodiment of the present disclosure, the method purifies crude IO-125 to provide a purity range of about 94 to 97%, preferably about 94 to 96.6% for the IO-125 compound.

The crystalline Form 1 of IO-125 can be in the form of a particle. As used herein, the term "particle" encompasses liposomes, emulsions, vesicles and lipid particles. Generally, the particle can be of any shape or form, e.g., spherical, rod, elliptical, cylindrical, capsule, or disc; and these particles can be part of a network or an aggregate. Without limitations, the particle can have any size from nm to millimeters. In some embodiments, the particle is a microparticle or a nanoparticle. As used herein, the term "microparticle" refers to a particle having a particle size of about 1 μm to about 1000 μm. As used herein, the term "nanoparticle" refers to particle having a particle size of about 0.1 nm to about 1000 nm. Generally, the particles disclosed herein are nanoparticles and have an average diameter of from about 5 nm to about 500 nm. In some embodiments, the particles have an average diameter of from about 75 nm to about 500 nm, from about 25 nm to about 250 nm, from about 50 nm to about 150 nm, from about 75 nm to about 125 nm, from about 50 nm to about 500 nm, from about 75 nm to about 200 nm, from about 100 to about 175 nm, from about 125 nm to about 175 nm, from about 40 nm to about 90 nm, or from about 50 nm to about 80 nm.

In some embodiments, a nanoparticle can be less than about 1 um in diameter, e.g., about 1 um or less in diameter, about 500 nm or less in diameter, about 400 nm or less in diameter, about 300 nm or less in diameter, about 200 nm or less in diameter, about 100 nm or less in diameter, about 50 nm or less in diameter, or about 10 nm or less in diameter. In some embodiments, a nanoparticle can be less than 1 um in diameter, e.g., 1 um or less in diameter, 500 nm or less in diameter, 400 nm or less in diameter, 300 nm or less in diameter, 200 nm or less in diameter, 100 nm or less in diameter, 50 nm or less in diameter, or 10 nm or less in diameter. In some embodiments, the nanoparticles in a composition can be from about 1 nm to about 1 um in diameter, e.g. from about 1 nm to about 500 nm in diameter, from about 1 nm to about 200 nm in diameter, from about 10 nm to about 200 nm in diameter, from about 100 nm to about 200 nm in diameter, or from about 10 nm to about 100 nm in diameter. In some embodiments, the nanoparticles in a composition can be from 1 nm to 1 um in diameter, e.g. from 1 nm to 500 nm in diameter, from 1 nm to 200 nm in diameter, from 10 nm to 200 nm in diameter, from 100 nm to 200 nm in diameter, or from 10 nm to 100 nm in diameter.

In some embodiments, nanoparticles can be selected to be of specific sizes, e.g. less than about 200 nm in diameter. Methods of selecting nanoparticles of a particular size and/or range of sizes are known in the art and can include, by way of non-limiting example, filtration, sedimentation, centrifugation, and/or chromatographic methods, e.g. SEC.

The present disclosure relates nanoparticle comprising crystalline Form 1 of compound IO-125.

In an embodiment of the present disclosure, the nanoparticle further comprises a co-lipid and/or stabilizer, wherein ratio of the compound to co-lipid and/or stabilizer ranges from 99:1 to 1:99 (w/w), (mol/mol) or (vol/vol).

In another embodiment of the present disclosure, the co-lipid is either Soy-phosphatidyl choline or 1,2-Distearoyl-sn-Glycero-3-Phosphoethalonamine-N-[Methoxy (Polyethylene glycol)-2000] or any combination thereof; and wherein the ratio of the compound and the co-lipids ranges from about 1:1:0.01 to about 1:4:3.

The present disclosure also provides composition(s) comprising the crystalline compound of IO-125 or a nanoparticle comprising the crystalline compound of IO-125, along with excipients.

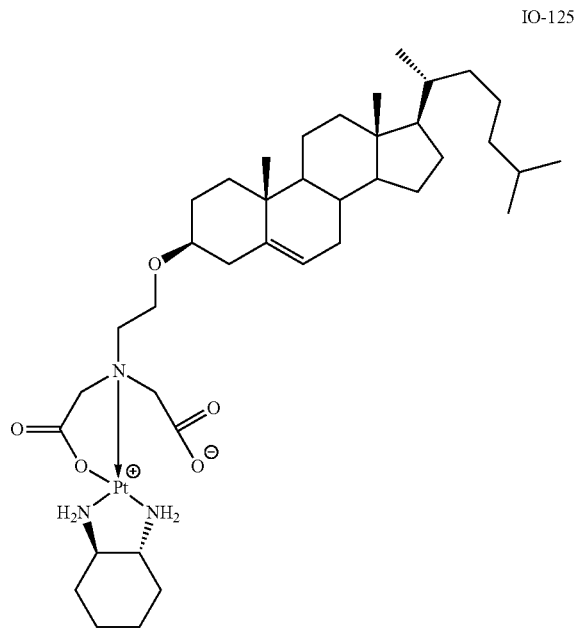

IO-125

In an embodiment of the present disclosure, the excipient is selected from a group consisting of granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material, spheronization agents, or any combination thereof.

In another embodiment of the present disclosure, the composition is formulated into dosage form selected from a group consisting of injectable, tablet, lyophilized powder, liposomal suspension, troches, lozenges, aqueous or oily suspensions, ointment, patch, gel, lotion, dentifrice, capsule, emulsion, creams, spray, drops, dispersible powders or granules, emulsion in hard or soft gel capsules, syrups, elixirs and food supplement, or any combination thereof.

The present disclosure also relates to a method of treating or managing cancer in a subject, the method comprising administering a therapeutically effective amount of a crystalline Form 1 of compound IO-125, or a nanoparticle of a crystalline Form 1 of compound IO-125, or a composition comprising a crystalline Form 1 of compound IO-125 or nanoparticle of a crystalline Form 1 of compound IO-125 to a subject in need thereof.

In an embodiment of the present disclosure, the cancer is selected from the group consisting of breast, head and neck, ovarian, testicular, pancreatic, oral-esophageal, gastrointestinal, liver, gall bladder, lung, melanoma, skin, sarcoma, blood, brain, glioblastoma, tumor of neuroectodermal origin and any combinations thereof.

In another embodiment of the present disclosure, the administration is via intravenous administration, intra articular administration, pancreatic duodenal artery administration, intraperitoneal administration, hepatoportal administration, intramuscular administration, or any combinations thereof.

The present disclosure further relates the use of a crystalline Form 1 of compound IO-125 or a nanoparticle of a crystalline Form 1 of compound IO-125, or a composition of said crystalline Form 1 of compound IO-125 in the manufacture of a medicament.

In an embodiment of the present disclosure, the crystalline Form 1 of compound IO-125 or a nanoparticle of a crystalline Form 1 of compound IO-125, or a composition of a crystalline Form 1 of compound IO-125 is used in the manufacture of a medicament for treating cancer selected from a group consisting of breast, head and neck, ovarian, testicular, pancreatic, oral-esophageal, gastrointestinal, liver, gall bladder, lung, melanoma, skin, sarcoma, blood, brain, glioblastoma, tumor of neuroectodermal origin and combinations thereof.

The present disclosure also relates a crystalline Form 1 of compound IO-125 a nanoparticle of a crystalline Form 1 of compound IO-125, or a composition of a crystalline Form 1 of compound IO-125 for use as a medicament.

In an embodiment of the present disclosure, the crystalline Form 1 of compound IO-125 a nanoparticle of a crystalline Form 1 of compound IO-125, or a composition of a crystalline Form 1 of compound IO-125 for use as a medicament in the treatment of cancer selected from a group consisting of breast, head and neck, ovarian, testicular, pancreatic, oral-esophageal, gastrointestinal, liver, gall bladder, lung, melanoma, skin, sarcoma, blood, brain, glioblastoma, tumor of neuroectodermal origin and combinations thereof.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

All the crystallographic experimental studies in the present disclosure/examples are carried out using 'Amorphous IO-125' (crude compound), which is characterised by 2θ diffractogram (FIG. 18), TG/DTA thermogram (FIG. 19) and HPLC chromatogram of IO-125 (FIG. 20).

Examples Showing Preparation of Crystalline Form 1 of Compound IO-125

Example 1

Crystallisation of Crude Compound 25 Using Methanol: Dichloromethane:
Crystallisation of crude compound 25 (COMP 25) is carried out using methanol:dichloromethane (20:80% v/v) and (10:90% v/v) solvent systems. XRPD 2θ diffractograms of solids recovered from successful crystallisation screening of crude COMP 25 are shown in FIG. 1.

Example 2

Seeded Cooling Crystallization of Crude COMP 25:
Approximately 20 mg of Crude COMP 25 is weighed into a 2 ml glass vial, and 100 microL of Methanol:dichloromethane (10:90% v/v) or Methanol:dichloromethane (20:80% v/v) solvent system is added to the experiments at ca. 25° C. All solvents are dried over pre-dried 3 A molecular sieves (where appropriate) prior to use. Small amount of crystalline COMP 25 is added as a seed to the experiments. The experiments are heated to about 40° C. The experiments are cooled down to about 5° C. at ca. 0.11° C./minute. The experiments are stirred at about 5° C. for about 3 hours and temperature cycled between about 5° C. to 40° C. at 0.2° C./minute overnight (ca. 18 hours). The solids materials are isolated using centrifuge at ambient (ca. 22° C.) and analysed by XRPD. Methanol:dichloromethane (10:90% v/v). Methanol:dichloromethane (20:80% v/v) returned weakly crystalline material. FIG. 2 shows XRPD 2θ diffractograms on solids after temperature cycling and FIG. 3 shows PLM micrographs of crystalline material obtained from seeded methanol:dichloromethane (10:90% v/v).

Example 3

Cooling Crystallization of Crude COMP 25 (20 mg Trial):
Crude COMP 25 is weighed into a 2 mL sample vial and a known aliquot of solvent (methanol:dichloromethane [10:90%]; ethanol:dichloromethane [10:90% or 20:80%]) added at ca. 25° C. The sample is stirred at 25° C., cooled down from 25° C. to 5° C. at ca. 0.11° C./minute, stirred again at about 5° C. for about 3 hours, and temperature cycled between about 5° C. to 40° C. at ca. 0.2° C./minutes. The solids are isolated at about 25° C. using centrifuge and analysed by XRPD. Table 4 (of protocol 4) summarizes the conditions used for cooling crystallization and Table 5 (of protocol 4) summarizes the conditions for cooling crystallisation in double scale. Tables 6 and 7 (of protocol 4) summarize the results and observations for the cooling crystallization studies. XRPD 2θ diffractograms of exemplary solids after temperature cycling at concentration ca. 150 mg/ml are shown in FIG. 4. And Table 12 shows XRPD peak table for 10-125, Form 1.

Example 4

Anti-Solvent/Cooling Crystallization of Crude COMP 25:
Approximately 50 mg COMP 25 Crude is weighed into a 2 mL sample vial and appropriate volume of respective solvent (methanol:dichloromethane [10:90% or 20:80% or 30:70%]; ethanol:dichloromethane [10:90% or 20:80%]) is added at ca. 25° C. Respective anti-solvent is added to appropriate vial in 25 microL aliquots at ca. 25° C. The experiments are cooled down from about 25° C. to 5° C. at ca. 0.11° C./minute, stirred at about 5° C. for about 3 hours. The experiments are temperature cycled between about 5° C. to 40° C. at ca. 0.2° C./minute overnight (ca. 18 hours). The experiments where thin slurry or clear solution are observed further anti-solvent is added to the experiments at ca. 25° C. The experiments are cooled down from about 25° C. to 5° C. at ca. 0.11° C./minute, again stirred at about 5° C. for about 3 hours. The experiments are temperature cycled overnight between about 5° C. to 40° C. at ca. 0.2° C./minute overnight (ca. 18 hours). The experiments where solid material is observed, the solids are isolated at ambient (ca. 22° C.) using centrifuge and analysed by XRPD. Samples that are isolated are then dried under vacuum at ambient temperature overnight. Using 2-methyl THF as an anti-solvent the crystallisations are resulted in formation of gel like material using methanol:dichloromethane solvent mixtures and ethanol:dichloromethane (30:70% v/v) solvent system. Using heptane as an anti-solvent crystalline material is observed using most of the solvent systems. As shown in Tables 8 and 9 [of protocol 5], using acetonitrile as an anti-solvent partially crystalline material is observed using most of the solvent systems. XRPD 2θ diffractograms of solids after temperature cycling, anti-solvent used heptanes are shown in FIGS. 5 and 6.

Example 5

Cooling Crystallization of Crude COMP 25 (200-250 mg Scale):

Respective mass of COMP 25 Crude is weighed into a 20 mL sample vial and appropriate volume of respective solvent system (methanol:dichloromethane [10:90% or 20:80%]) is added at ca. 25° C. to dissolve the sample. The experiments are cooled down to about 5° C. at ca. 0.1° C./min, stirred at 5° C. for 2 hours, temperature cycled between about 5° C. to 40° C., heated to about 40° C. over about 2 hours (ca. 0.3° C./minute). The sample is again stirred at about 40° C. for about 2 hours, cooled down to about 5° C. over about 2 hours (ca. 0.3° C./minute). The sample is further stirred at about 5° C. for about 2 hours. Samples are isolated at ambient (ca. 22° C.) by filtering over Buchner funnel under vacuum using Whatmann filter paper No. 1, then dried under vacuum at ambient temperature overnight (approx. 18 hrs). The solid material is then analysed by XRPD and PLM. Results are summarized in Table 10 (refer protocol 6) and shown in FIGS. 7 and 8. HPLC chromatogram of an exemplary cooling crystallization 2 is shown in FIG. 9.

Example 6

Seeded Cooling Crystallization of Crude COMP 25 (250 mg Scale):

Respective mass of Crude COMP 25 is weighed into a 20 mL sample vial and appropriate volume of respective solvent system (methanol:dichloromethane [10:90% or 20:80%]) is added at ca. 25° C. to dissolve the sample. Crystalline COMP 25 is added to the experiments as a seed. The experiments are cooled down to about 5° C. at ca. 0.1° C./min, stirred at about 5° C. for about 2 hours, temperature cycled between about 5° C. to 40° C., heated to about 40° C. over about 2 hours (ca. 0.3° C./minute), stirred at about 40° C. for about 2 hours, cooled down to about 5° C. over about 2 hours (ca. 0.3° C./minute) and stirred again at about 5° C. for about 2 hours. Samples are isolated at ambient (ca. 22° C.) by filtering over Buchner funnel under vacuum using Whatmann filter paper No. 1, then dried under vacuum at ambient temperature overnight (ca. 18 hours). The solid material is then analysed by XRPD and PLM. Results are summarized in Table 11 (refer protocol 7) and shown in FIGS. 10 and 11.

Solvent mixture methanol:dichloromethane (10:90% v/v) at Concentration 160 mg/ml: The material returned is crystalline and had a purity of about 96.65% by HPLC. The calculated yield for this experiment is about 36%.

Solvent mixture methanol:dichloromethane (20:80% v/v) at Concentration 190 mg/ml: The material returned is crystalline and had a purity of about 96.21% by HPLC (FIG. 12). The calculated yield for this experiment is about 41%.

Example 7

Seeded, Anti-Solvent and Cooling Crystallization:

Approximately 250 mg Crude COMP 25 is weighed into a 20 mL sample vial and appropriate volume of respective solvent system (methanol:dichloromethane [10:90% or 20:80%]) is added at ca. 25° to dissolve the IO-125. Heptane is added as an anti-solvent in about 250 microL aliquots. Total about 1 ml heptane is added to each experiment. The experiments are seeded using crystalline COMP 25 (approx. 5 mg). The experiments are stirred at about 25° C. for ca. 1 hour and then cooled down to about 5° C. at ca. 0.1° C./minute, stirred at about 5° C. for about 2 hours, temperature cycled between about 5° C. to 40° C., heated to about 40° C. over about 2 hours (ca. 0.3° C./minute), stirred at about 40° C. for about 2 hours, cooled down to about 5° C. over about 2 hours (ca. 0.3° C./minute) and again stirred at about 5° C. for about 2 hours. The experiments are isolated at ambient (ca. 22° C.) by filtering over Buchner funnel under vacuum using Whatmann filter paper no 1 and then dried under vacuum at ambient temperature overnight (ca. 18 hours). The solid material is then analysed by XRPD (FIG. 13) and PLM (FIG. 14). The combination of all three techniques was used to see if there was any difference in the material produced from solvent systems and also to assess the best crystallisation conditions. Yield calculations were carried out and are summarized in Table 12 (refer protocol 8). HPLC chromatogram of an isolated solid using methanol:dichloromethane (20:80% v/v) with heptanes as anti-solvent is shown in FIG. 15.

The XRPD peak table of the present crystalline IO-125 (Form 1) is provided in Table 13.

TABLE 13

XRPD peak table for Crystalline IO-125, Form 1.

| No. | Pos. [°2Th.] | FWHM [°2Th.] | Area [cts * °2Th.] | d-spacing [Å] | Height [cts] | Rel. Int. [%] |
|---|---|---|---|---|---|---|
| 1 | 3.16 | 0.12 | 948.08 | 27.93 | 8348.13 | 100.00 |
| 2 | 6.34 | 0.10 | 293.30 | 13.93 | 2905.46 | 34.80 |
| 3 | 9.12 | 0.09 | 109.02 | 9.70 | 1234.25 | 14.78 |
| 4 | 9.54 | 0.12 | 81.34 | 9.27 | 716.22 | 8.58 |
| 5 | 10.66 | 0.12 | 75.86 | 8.30 | 667.98 | 8.00 |
| 6 | 12.95 | 0.09 | 147.99 | 6.84 | 1675.40 | 20.07 |
| 7 | 13.57 | 0.08 | 38.56 | 6.53 | 509.27 | 6.10 |
| 8 | 14.02 | 0.09 | 136.15 | 6.31 | 1541.37 | 18.46 |
| 9 | 14.86 | 0.10 | 16.96 | 5.96 | 167.99 | 2.01 |
| 10 | 15.55 | 0.09 | 173.66 | 5.70 | 1966.01 | 23.55 |
| 11 | 16.06 | 0.10 | 37.12 | 5.52 | 367.75 | 4.41 |
| 12 | 16.45 | 0.12 | 253.50 | 5.39 | 2232.13 | 26.74 |
| 13 | 17.45 | 0.13 | 669.02 | 5.08 | 5301.79 | 63.51 |
| 14 | 18.31 | 0.08 | 117.01 | 4.85 | 1545.44 | 18.51 |
| 15 | 18.76 | 0.13 | 42.43 | 4.73 | 336.22 | 4.03 |
| 16 | 19.58 | 0.23 | 80.45 | 4.53 | 354.18 | 4.24 |
| 17 | 20.75 | 0.15 | 43.88 | 4.28 | 289.75 | 3.47 |
| 18 | 21.56 | 0.12 | 464.92 | 4.12 | 2794.01 | 33.47 |
| 19 | 21.63 | 0.10 | 332.31 | 4.11 | 3291.80 | 39.43 |
| 20 | 21.92 | 0.10 | 76.03 | 4.05 | 753.15 | 9.02 |
| 21 | 22.22 | 0.10 | 32.78 | 4.00 | 324.70 | 3.89 |
| 22 | 23.22 | 0.14 | 116.55 | 3.83 | 839.66 | 10.06 |
| 23 | 24.01 | 0.13 | 37.67 | 3.71 | 298.50 | 3.58 |
| 24 | 24.62 | 0.15 | 39.28 | 3.62 | 259.42 | 3.11 |
| 25 | 25.52 | 0.15 | 22.75 | 3.49 | 150.22 | 1.80 |
| 26 | 26.07 | 0.13 | 29.87 | 3.42 | 236.70 | 2.84 |
| 27 | 26.42 | 0.31 | 49.03 | 3.37 | 161.89 | 1.94 |
| 28 | 27.16 | 0.20 | 22.93 | 3.28 | 113.58 | 1.36 |
| 29 | 27.50 | 0.15 | 23.61 | 3.24 | 155.89 | 1.87 |
| 30 | 27.89 | 0.15 | 30.70 | 3.20 | 202.71 | 2.43 |
| 31 | 28.28 | 0.15 | 22.73 | 3.16 | 150.08 | 1.80 |
| 32 | 29.03 | 0.15 | 29.82 | 3.08 | 196.94 | 2.36 |
| 33 | 29.78 | 0.15 | 49.00 | 3.00 | 323.60 | 3.88 |
| 34 | 31.35 | 0.26 | 45.69 | 2.85 | 181.04 | 2.17 |
| 35 | 31.65 | 0.15 | 15.06 | 2.83 | 99.46 | 1.19 |
| 36 | 32.26 | 0.23 | 50.66 | 2.78 | 223.02 | 2.67 |
| 37 | 32.95 | 0.20 | 17.14 | 2.72 | 84.88 | 1.02 |
| 38 | 33.28 | 0.20 | 37.27 | 2.69 | 184.61 | 2.21 |
| 39 | 33.77 | 0.20 | 10.62 | 2.65 | 52.61 | 0.63 |

Example 7

Crystallization Using Organic Acid and Halogenated Hydrocarbon Solvent:

38.0 g crude dried IO-125 is charged with about 4 w/w water. After stirring for about 1.5 h at about 70° C., cooling and addition of about 16 w/w acetone is performed, and 35.8 g crystallized IO-125 is isolated by filtration and washing with about 1 w/w water. The slurry is repeated once again delivering 34.4 g crude dried product after drying under vacuum at about 50° C. This was in turn dissolved in about 26.5 w/w dichloromethane and about 1 w/w acetic acid and the solution filtered (polish).

After addition of about 10 w/w ethanol and distillation to about 8.6 v/w, the crystallized wet product (32.3 g) is isolated by filtration and washing with about 1 w/w ethanol. Drying vacuum at about 40° C. afforded about 21.8 g of crystallised dried product. IPC showed about 1.68% w/w of acetic acid. In order to reduce its amount, an additional slurry was performed on about 17.8 g, delivering 16.3 g of material with 0.23% acetic acid content. Table 14 provides analytical results of trial IO-125 crystalline forms.

Accordingly, the present disclosure has been able to achieve crystalline form of lipid-based platinum-based compound, especially IO-125 compound. Extensive experimentations using numerous crystallization conditions lead to the specific crystal Form 1 of compound IO-125. The present method is simple, cost-effective, commercially scalable, with good shelf-life properties, easy to handle, and the crystal product can be employed in various medical conditions including cancer.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that this invention is not limited to the particular methodology, protocols, and reagents, etc., described herein and as such may vary. The terminology

TABLE 14

Analytical results of trial IO-125 crystalline forms

| Analysis | Specifications | Results |
| --- | --- | --- |
| Assay Pt (ICP OES) | Report Result | 21.43% |
| Purity (HPLC) | >96% | 96.35% |
| Assay (anhydrous-solvent free) | 90-110 | 92.8% |
| Residual solvents (GC-HS) | Acetone NMT 5000 ppm | Acetone: 260 ppm |
| | Ethanol NMT 5000 ppm | Ethanol: not detected |
| | DCM NMT 600 ppm | DCM: not detected |
| | THF NMT 720 ppm | THF: not detected |
| | Acetic acid NMT 5000 ppm | Acetic acid <1000 ppm |
| Water content (KF) | Report result | 1.23% |
| Elemental Impurities | Report Results, all within below toxic limits | As <0.15 µg/g |
| | | Cd <0.2 µg/g |
| | | Hg <0.15 µg/g |
| | | Pb <0.5 µg/g |
| | | Ir <0.5 µg/g |
| | | Os <0.5 µg/g |
| | | Pd <0.5 µg/g |
| | | Rh <0.5 µg/g |
| | | Ru <0.5 µg/g |
| | | Cr <0.5 µg/g |
| | | Mo <0.5 µg/g |

The invention claimed is:

1. A crystalline form 1 of compound IO-125 having an X-ray powder diffractogram pattern comprising peaks at diffraction angles 2θ of 3.16, 6.34, 12.95, 15.55, 16.45, 17.4, 21.56 and 21.92°

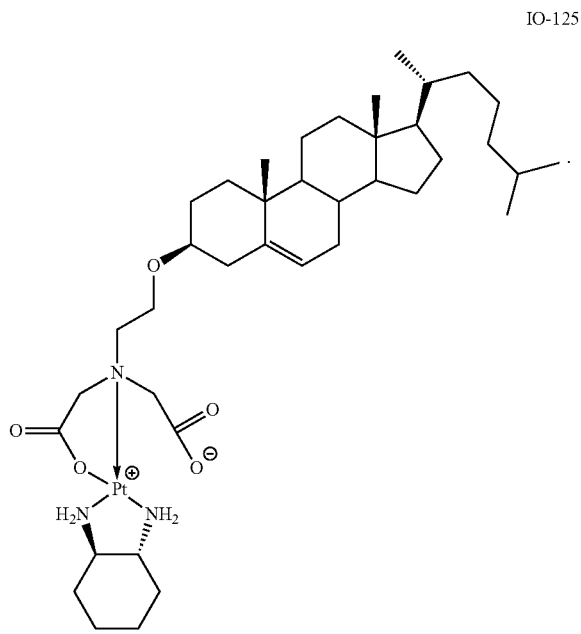

IO-125

2. The crystalline form 1 of claim 1, having a melting point of about 320° C. and purity of about 97%.

Figure 10:
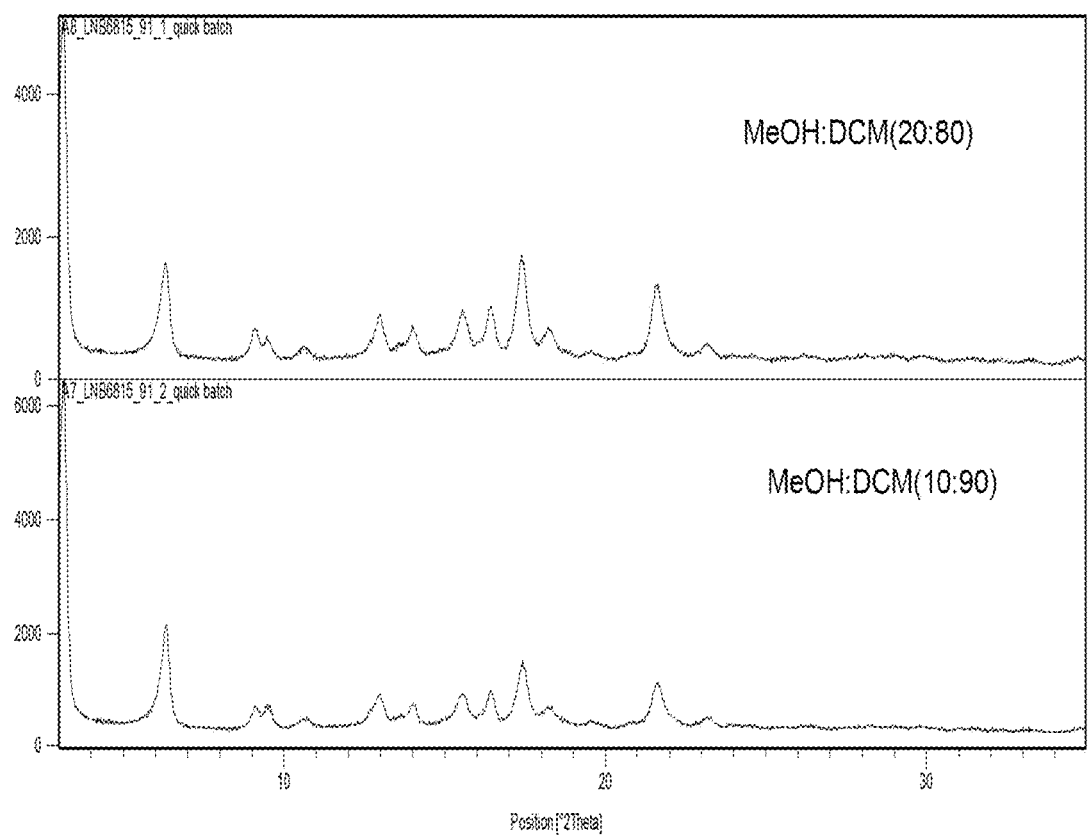
FIGS. 10 and 11 show XRPD 2θ diffractograms and PLM of solids obtained by way of protocol 7.
Figure 11:
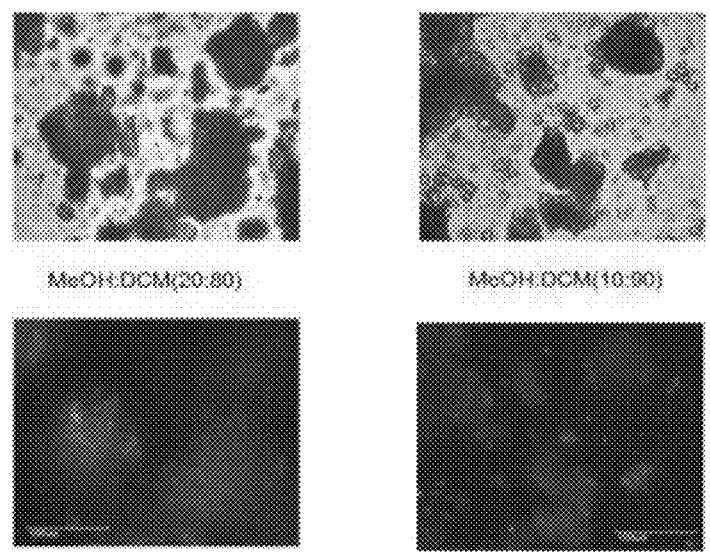
Figure 16:
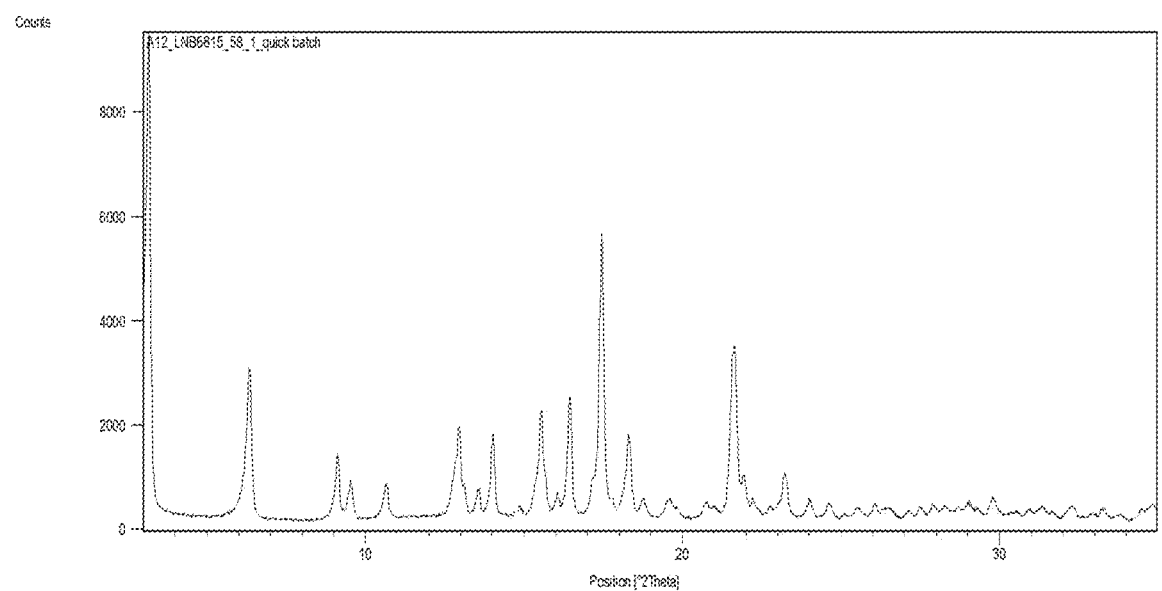
FIG. 16 shows IO-125, Form 1 2θ diffractogram.

3. The crystalline form 1 of that is characterized by:
   (i) a powder X-ray diffraction spectrum substantially as shown in FIG. 4;
   (ii) a powder X-ray diffraction spectrum substantially as shown in FIG. 5;
   (iii) a powder X-ray diffraction spectrum substantially as shown in FIG. 10;
   (iv) a powder X-ray diffraction spectrum substantially as shown in FIG. 13;
   (v) a powder X-ray diffraction spectrum substantially as shown in FIG. 16;
   (vi) a coupled thermogravimetric/differential thermal analysis thermogram substantially as shown in FIG. 17;
   (vii) a high performance liquid chromatography chromatogram substantially as shown in FIG. 15.

4. A method for preparing the crystalline Form 1 of claim 1, comprising:
   (i) dissolving crude IO-125 in at least one solvent to form a solution;
   (ii) crystallizing the crystalline Form 1 from the solution; and
   (iii) optionally repeating step (ii).

5. The method of claim 4, wherein the solvent is a lower alkyl alcohol, halogenated hydrocarbon, inorganic solvent, an organic solvent or a combination thereof.

6. The method of claim 5, wherein the lower alkyl alcohol is methanol, ethanol, propanol, isopropanol, butanol, isobutanol, pentanol, iso-pentanol, or a combination thereof; the halogenated hydrocarbon solvent is dichloromethane, chloroform, or a combination thereof; the inorganic solvent is water; and the organic solvent is dimethylformamide.

7. The method of claim 4, wherein the solvent is a methanol and dichloromethane mixture, methanol and chloroform mixture, ethanol and dichloromethane mixture, ethanol and chloroform mixture, or a combination thereof.

8. The method of claim 4, wherein the solvent is chloroform, a methanol and dichloromethane mixture having a concentration ratio from about 10:90 to 90:10, by volume; a methanol and chloroform mixture having a concentration ratio from about 10:90 to 90:10, by volume; an ethanol and dichloromethane mixture having a concentration ratio from about 10:90 to 90:10, by volume; or an ethanol and chloroform mixture having a concentration ratio from about 10:90 to 90:10, by volume.

9. The method of claim 8, wherein the solvent is a methanol and dichloromethane mixture having a concentration ratio of about 10:90, by volume; a methanol and chloroform mixture having a concentration ratio of about 10:90, by volume; an ethanol and dichloromethane mixture having a concentration ratio of about 10:90, by volume; or an ethanol and chloroform mixture having a concentration ratio of about 10:90, by volume.

10. The method of claim 4, wherein the crystallizing is performed by controlled linear cooling of the IO-125 solution, changing the temperature, adding an anti-solvent, evaporating and seeding, or a combination thereof.

11. The method of claim 10, wherein the anti-solvent is heptane, acetonitrile, or a combination thereof.

12. The method of claim 4, wherein the at least one solvent is a mixture of a lower alkyl alcohol and halogenated hydrocarbon solvent system.

13. The method of claim 4, wherein the crystallizing comprises adding a seed of crystalline Form 1 of IO-125 to the solution, followed by heating and cooling.

14. The method of claim 4, wherein the crystallizing comprises cooling and temperature cycling.

15. The method of claim 4, wherein the crystallizing comprises adding anti-solvent to the solution followed by cooling and temperature cycling.

16. The method of claim 4, wherein the crystallizing comprises adding anti-solvent and a seed of crystalline Form 1 to the solution, cooling and temperature cycling, followed by heating and cooling the solution.

17. The method of claim 12, wherein the lower alkyl alcohol is methanol or ethanol; the halogenated hydrocarbon solvent is dichloromethane or chloroform; and wherein the concentration ratio of lower alkyl alcohol to halogenated hydrocarbon solvent is in a range of from about 10:90 to 30:70, by volume.

18. The method of claim 4, further comprising isolating the crystalline Form 1.

19. The method of claim 18, wherein the isolating is performed by adding solvent to the solution, distilling, heating, adding an ionic resin, quenching, filtering, extracting, or a combination thereof.

20. The method of claim 4, that is performed at a temperature in a range from about 0° C. to 80° C. for a time period in a range from about one hour to 48 hours; and the linear cooling is performed at 5° C. at a rate of 0.11° C./mins.

21. The method of claim 4, wherein the crystalline Form 1 has a purity of about 94 to 97%.

22. The crystalline form 1 of claim 1, characterized by a coupled thermogravimetric/differential thermal analysis thermogram showing a loss of about 2.9 w/w % from 25° C. to 160° C.

23. The crystalline form 1 of claim 1, wherein the an X-ray powder diffractogram pattern further comprises one or more peaks at diffraction angles 2θ of 9.12, 14.02, 18.31, 21.63, 23.22, 24.01, or 29.03°.

* * * * *